(12) United States Patent
Schroth et al.

(10) Patent No.: US 6,355,428 B1
(45) Date of Patent: *Mar. 12, 2002

(54) NUCLEIC ACID LIGAND INTERACTION ASSAYS

(75) Inventors: Gary P. Schroth, Foster City; Thomas Wayne Bruice, Carlsbad; Young J. Suh, Union City, all of CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/393,783

(22) Filed: Sep. 10, 1999

Related U.S. Application Data

(63) Continuation-in-part of application No. 09/151,890, filed on Sep. 11, 1998.

(51) Int. Cl.[7] .......................... C12Q 1/68; G01N 33/566
(52) U.S. Cl. .............................. 435/6; 935/77; 935/78; 436/501
(58) Field of Search ..................... 435/6, 810; 436/501; 935/77, 78

(56) References Cited

U.S. PATENT DOCUMENTS

| | | |
|---|---|---|
| 4,382,074 A | 5/1983 | Hart |
| 5,635,347 A | 6/1997 | Link et al. |
| 5,705,402 A | 1/1998 | Leland et al. |
| 5,747,254 A | 5/1998 | Pontius |
| 5,770,459 A | 6/1998 | Massey et al. |
| 5,853,986 A | 12/1998 | Petrie, III et al. |

FOREIGN PATENT DOCUMENTS

| | | |
|---|---|---|
| EP | 446 245 B1 | 5/1999 |
| WO | WO 95/00666 | 1/1995 |
| WO | WO 97/09342 | 3/1997 |
| WO | WO 98/10096 | 3/1998 |

OTHER PUBLICATIONS

Cardullo, R.A., et al., "Detection of nucleic acid hybridization by nonradiative fluorescense resonance energy transfer" *Proc. Natl. Acad. Sci.* USA 85:8790–8794 (1988).

Chen, Q., et al., "Structure–Based Discovery of Ligands Targeted to the RNA Double Helix" *Biochemistry* 36:11402–11407 (1997).

Diebold, R.J., et al., "Molecular basis of cooperative DNA bending and oriented heterodimer binding in the NFAT1–Fos–Jun–ARRE2 complex" *Proc. Natl. Acad. Sci.* USA 95(14):7915–7920 (1988).

Matthews, J.A. and Kricka, L.J., "Analytical Strategies for the use of DNA probes" *Analytical Biochem* 169:1–25 (1988).

Wilson, D.W., et al., "Evaluation of Drug–Nucleic Acid Interactions by Thermal Melting Curves" *Methods in Molecular.*

*Biology vol. 90:Drug–DNA Interaction Protocols* K.R. Fox (ed.) Humana Press Inc. Totowa NJ pp. 219–231, 1997.

Primary Examiner—Marianne P. Allen
(74) Attorney, Agent, or Firm—LeeAnn Gorthey

(57) ABSTRACT

Methods for determining the relative binding affinities of various ligands to various nucleic acid sequences, particularly in double stranded form, are described. In a direct binding assay, the effect of adding increasing amounts of a ligand on a signal generated by two "indicator" oligonucleotides is observed. Also described is a competitive binding assay, in which a competitor oligonucleotide is added to an indicator duplex having a ligand bound thereto. The assays allow the rapid and convenient determination of nucleic acid binding specificities and base pair determinants of specificity of particular ligands.

38 Claims, 21 Drawing Sheets

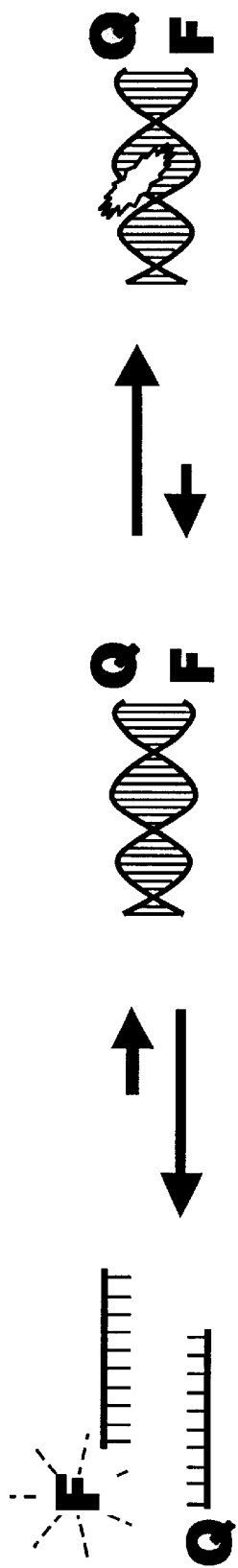
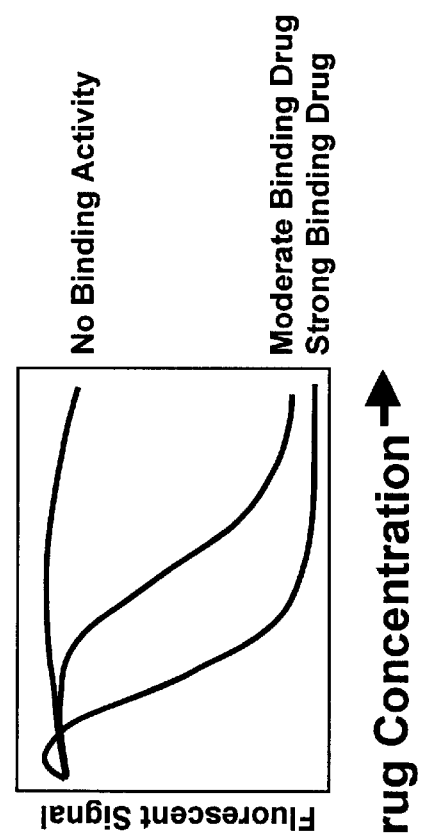
Fig. 1A
Fig. 1B

SEQUENCE LISTING

```
<160> NUMBER OF SEQ ID NOS: 80

<210> SEQ ID NO 1
<211> LENGTH: 10
<212> TYPE: DNA
<213> ORGANISM: Artificial Sequence
<220> FEATURE:
<221> NAME/KEY: misc_binding
<222> LOCATION: (1)...(10)
<223> OTHER INFORMATION: Synthesized test oligonucleotide for binding
      studies

<400> SEQUENCE: 1
cttttttttt                                                              10

<210> SEQ ID NO 2
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 2
ctttattatt tt                                                           12

<210> SEQ ID NO 3
<211> LENGTH: 9
<212> TYPE: DNA
<213> ORGANISM: Artificial Sequence
<220> FEATURE:
<221> NAME/KEY: misc_binding
<222> LOCATION: (1)...(9)
<223> OTHER INFORMATION: synthesized test oligonucleotide for binding
      studies

<400> SEQUENCE: 3 ctctctctc                                                                9

<210> SEQ ID NO 4
<211> LENGTH: 10
<212> TYPE: DNA
<213> ORGANISM: Artificial Sequence
<220> FEATURE:
<221> NAME/KEY: modified_base
<222> LOCATION: (3)...(4)
<223> OTHER INFORMATION: I
<221> NAME/KEY: modified_base
```

```
<222> LOCATION: (7)...(8)
<223> OTHER INFORMATION: I
<221> NAME/KEY: misc_binding
<222> LOCATION: (1)...(10)
<223> OTHER INFORMATION: synthesized test oligonucleotide for binding
      studies

<400> SEQUENCE: 4 ccnnccnncc                                                              10

<210> SEQ ID NO 5
<211> LENGTH: 10
<212> TYPE: DNA
<213> ORGANISM: Artificial Sequence
<220> FEATURE:
<221> NAME/KEY: modified_base
<222> LOCATION: (5)...(6)
<223> OTHER INFORMATION: I
<221> NAME/KEY: misc_binding
<222> LOCATION: (1)...(10)
<223> OTHER INFORMATION: synthesized oligonucleotide for ligand binding
      studies

<400> SEQUENCE: 5 ggccnnccgg                                                              10

<210> SEQ ID NO 6
<211> LENGTH: 7
<212> TYPE: DNA
<213> ORGANISM: Artificial Sequence
<220> FEATURE:
<221> NAME/KEY: misc_binding
<222> LOCATION: (1)...(7)
<223> OTHER INFORMATION: synthesized test oligonucleotide for ligand
      studies

<400> SEQUENCE: 6 ccgcgcc                                                                  7

<210> SEQ ID NO 7
<211> LENGTH: 6
<212> TYPE: DNA
<213> ORGANISM: Artificial Sequence
<220> FEATURE:
<221> NAME/KEY: misc_binding
<222> LOCATION: (1)...(6)
<223> OTHER INFORMATION: synthesized test oligonucleotide for binding
      studies

<400> SEQUENCE: 7 cgcgcg                                                                   6

<210> SEQ ID NO 8
<211> LENGTH: 7
<212> TYPE: DNA
<213> ORGANISM: Artificial Sequence
<220> FEATURE:
<221> NAME/KEY: misc_binding
<222> LOCATION: (1)...(7)
<223> OTHER INFORMATION: synthesized test oligonucleotide for binding
      studies

<400> SEQUENCE: 8 ccccccc                                                                  7

<210> SEQ ID NO 9
<211> LENGTH: 11
<212> TYPE: DNA
<213> ORGANISM: Artificial Sequence
```

```
<220> FEATURE:
<221> NAME/KEY: misc_binding
<222> LOCATION: (1)...(11)
<223> OTHER INFORMATION: synthesized test oligonucleotide for binding
      studies

<400> SEQUENCE: 9
gatatatata g                                                              11

<210> SEQ ID NO 10
<211> LENGTH: 8
<212> TYPE: DNA
<213> ORGANISM: Artificial Sequence
<220> FEATURE:
<221> NAME/KEY: misc_binding
<222> LOCATION: (1)...(8)
<223> OTHER INFORMATION: synthesized test oligonucleotide for binding
      studies

<400> SEQUENCE: 10 ggtattcg                                                                   8

<210> SEQ ID NO 11
<211> LENGTH: 8
<212> TYPE: DNA
<213> ORGANISM: Artificial Sequence
<220> FEATURE:
<221> NAME/KEY: misc_binding
<222> LOCATION: (1)...(8)
<223> OTHER INFORMATION: synthesized test oliognucleotide for binding
      studies

<400> SEQUENCE: 11 gcgtattt                                                                   8

<210> SEQ ID NO 12
<211> LENGTH: 9
<212> TYPE: DNA
<213> ORGANISM: Artificial Sequence
<220> FEATURE:
<221> NAME/KEY: misc_binding
<222> LOCATION: (1)...(9)
<223> OTHER INFORMATION: synthesized test oligonucleotide for binding
      studies

<400> SEQUENCE: 12 gcggtattt                                                                  9

<210> SEQ ID NO 13
<211> LENGTH: 6
<212> TYPE: DNA
<213> ORGANISM: Artificial Sequence
<220> FEATURE:
<221> NAME/KEY: misc_signal
<222> LOCATION: (1)...(6)
<223> OTHER INFORMATION: synthesized test oligonucleotide for binding
      studies.

<400> SEQUENCE: 13 cgcgcc                                                                     6

<210> SEQ ID NO 14
<211> LENGTH: 14
<212> TYPE: RNA
<213> ORGANISM: Artificial Sequence
<220> FEATURE:
<221> NAME/KEY: misc_binding
<222> LOCATION: (1)...(14)
<223> OTHER INFORMATION: synthesized test oligonucleotide for binding
``` studies

<400> SEQUENCE: 14
caugaucuga acuu    14

<210> SEQ ID NO 15
<211> LENGTH: 14
<212> TYPE: RNA
<213> ORGANISM: Artificial Sequence
<220> FEATURE:
<221> NAME/KEY: misc_binding
<222> LOCATION: (1)...(14)
<223> OTHER INFORMATION: synthesized test oligonucleotide for bindng
      studies

<400> SEQUENCE: 15
aaguucagau cuag    14

<210> SEQ ID NO 16
<211> LENGTH: 12
<212> TYPE: RNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 16
guucagaucu ag    12

<210> SEQ ID NO 17
<211> LENGTH: 10
<212> TYPE: RNA
<213> ORGANISM: Artificial Sequence
<220> FEATURE:
<221> NAME/KEY: misc_binding
<222> LOCATION: (1)...(10)
<223> OTHER INFORMATION: synthesized test oligonucleotide for binding
      studies

<400> SEQUENCE: 17
ucagaucuag    10

<210> SEQ ID NO 18
<211> LENGTH: 9
<212> TYPE: RNA
<213> ORGANISM: Artificial Sequence
<220> FEATURE:
<221> NAME/KEY: misc_binding
<222> LOCATION: (1)...(9)
<223> OTHER INFORMATION: synthesized test oligonucleotide for binding
      studies

<400> SEQUENCE: 18 cagaucuag    9

<210> SEQ ID NO 19
<211> LENGTH: 14
<212> TYPE: DNA
<213> ORGANISM: Artificial Sequence
<220> FEATURE:
<221> NAME/KEY: misc_binding
<222> LOCATION: (1)...(14)
<223> OTHER INFORMATION: synthesized test oligonucleotide for binding
      studies

<400> SEQUENCE: 19
ctagatctga actt                                                        14

<210> SEQ ID NO 20
<211> LENGTH: 14
<212> TYPE: DNA
<213> ORGANISM: Artificial Sequence
<220> FEATURE:
<221> NAME/KEY: misc_binding
<222> LOCATION: (1)...(14)
<223> OTHER INFORMATION: synthesized test oligonucleotide for binding
      studies

<400> SEQUENCE: 20
aagttcagat ctag                                                        14

<210> SEQ ID NO 21
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 21
gttcagatct ag                                                          12

<210> SEQ ID NO 22
<211> LENGTH: 10
<212> TYPE: DNA
<213> ORGANISM: Artificial Sequence
<220> FEATURE:
<221> NAME/KEY: misc_binding
<222> LOCATION: (1)...(10)
<223> OTHER INFORMATION: synthesized test oligonucleotide for binding
      studies

<400> SEQUENCE: 22
tcagatctag                                                             10

<210> SEQ ID NO 23
<211> LENGTH: 10
<212> TYPE: RNA
<213> ORGANISM: Artificial Sequence
<220> FEATURE:
<221> NAME/KEY: misc_binding
<222> LOCATION: (1)...(10)
<223> OTHER INFORMATION: synthesized test oligonucleotide for binding
      studies

<400> SEQUENCE: 23
cuagaucuga                                                             10

<210> SEQ ID NO 24
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 24
ctagatctga ac                                                          12

<210> SEQ ID NO 25

```
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 25
cccggccggc cc                                                           12

<210> SEQ ID NO 26
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 26
cccggacggc cc                                                           12

<210> SEQ ID NO 27
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 27
cccggaaccg cc                                                           12

<210> SEQ ID NO 28
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 28
cccggtaccg cc                                                           12

<210> SEQ ID NO 29
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 29
cccgaaaccg cc                                                           12

<210> SEQ ID NO 30
<211> LENGTH: 12
<212> TYPE: DNA
<213> ORGANISM: Artificial Sequence
<220> FEATURE:
```

```
<221> NAME/KEY: misc_binding
<222> LOCATION: (1)...(12)
<223> OTHER INFORMATION: synthesized test oligonucleotide for binidng
      studies

<400> SEQUENCE: 30
cccgataccg cc                                                              12

<210> SEQ ID NO 31
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 31
cccgaaaacg cc                                                              12

<210> SEQ ID NO 32
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 32
cccgatatcg cc                                                              12

<210> SEQ ID NO 33
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 33
cccaaaaagg cc                                                              12

<210> SEQ ID NO 34
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 34
ccctatatcg cc                                                              12

<210> SEQ ID NO 35
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies
```

```
<400> SEQUENCE: 35
cccaaaaaag cc                                                              12

<210> SEQ ID NO 36
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 36
ccctatatag cc                                                              12

<210> SEQ ID NO 37
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 37
ccaaaaaaag cc                                                              12

<210> SEQ ID NO 38
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 38
ccatatatag cc                                                              12

<210> SEQ ID NO 39
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 39
ccaaaaaaaa cc                                                              12

<210> SEQ ID NO 40
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 40
ccatatatat cc                                                              12
```

<210> SEQ ID NO 41
<211> LENGTH: 13
<212> TYPE: DNA
<213> ORGANISM: Artificial Sequence
<220> FEATURE:
<221> NAME/KEY: misc_binding
<222> LOCATION: (1)...(13)
<223> OTHER INFORMATION: synthesized test oligonucleotide for binding
      studies

<400> SEQUENCE: 41
gtgtgtgtgt gtg                                                    13

<210> SEQ ID NO 42
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 42
cccggccggc cc                                                     12

<210> SEQ ID NO 43
<211> LENGTH: 13
<212> TYPE: DNA
<213> ORGANISM: Artificial Sequence
<220> FEATURE:
<221> NAME/KEY: misc_binding
<222> LOCATION: (1)...(13)
<223> OTHER INFORMATION: synthesized test oligonculetoide for binding
      studies

<400> SEQUENCE: 43
ctctctctct ctc                                                    13

<210> SEQ ID NO 44
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 44
catgtcagtc ga                                                     12

<210> SEQ ID NO 45
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonuclotide for binding
      studies

<400> SEQUENCE: 45
ggaaggaagg aa                                                     12

<210> SEQ ID NO 46
<211> LENGTH: 12

```
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 46
cccgaaaacg cc                                                          12

<210> SEQ ID NO 47
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 47
cccgaattcg cc                                                          12

<210> SEQ ID NO 48
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 48
cccgtatacg cc                                                          12

<210> SEQ ID NO 49
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 49
cccgatatcg cc                                                          12

<210> SEQ ID NO 50
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 50
cccgttaacg cc                                                          12

<210> SEQ ID NO 51
<211> LENGTH: 12
<212> TYPE: DNA
<213> ORGANISM: Artificial Sequence
<220> FEATURE:
<221> NAME/KEY: misc_binding
```

```
<222> LOCATION: (1)...(12)
<223> OTHER INFORMATION: synthesized test oligonucletoide for binding
      studies

<400> SEQUENCE: 51
cccgtgttcg cc                                                          12

<210> SEQ ID NO 52
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 52
cccgaaaaac cg                                                          12

<210> SEQ ID NO 53
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 53
cccgaaattc cg                                                          12

<210> SEQ ID NO 54
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 54
cccgatatac cg                                                          12

<210> SEQ ID NO 55
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 55
cccgaataac cg                                                          12

<210> SEQ ID NO 56
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies
```

```
<400> SEQUENCE: 56
cccgtaaatc cg                                                      12

<210> SEQ ID NO 57
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 57
cccgataaac cg                                                      12

<210> SEQ ID NO 58
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 58
cccgttaaac cg                                                      12

<210> SEQ ID NO 59
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 59
cccgattaac cg                                                      12

<210> SEQ ID NO 60
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 60
cccgaattac cg                                                      12

<210> SEQ ID NO 61
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 61
cccgtaaaac cg                                                      12
```

<210> SEQ ID NO 62
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 62
cccgaaaatc cg                                                            12

<210> SEQ ID NO 63
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 63
cccgataaac cg                                                            12

<210> SEQ ID NO 64
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 64
ccccaattcg cc                                                            12

<210> SEQ ID NO 65
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 65
ccccaattag cc                                                            12

<210> SEQ ID NO 66
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 66
cccaaattgg cc                                                            12

<210> SEQ ID NO 67
<211> LENGTH: 12
<212> TYPE: DNA

<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 67
ccccaattgg cc                                                              12

<210> SEQ ID NO 68
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 68
cccaaattcg cc                                                              12

<210> SEQ ID NO 69
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 69
cccaaattag cc                                                              12

<210> SEQ ID NO 70
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 70
cccaaatttg cc                                                              12

<210> SEQ ID NO 71
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 71
cccgaattag cc                                                              12

<210> SEQ ID NO 72
<211> LENGTH: 12
<212> TYPE: DNA
<213> ORGANISM: Artificial Sequence
<220> FEATURE:
<221> NAME/KEY: misc_binding
<222> LOCATION: (1)...(12)

```
<223> OTHER INFORMATION: synthesized test oligonucleotide for binding
      studies

<400> SEQUENCE: 72
ccctaattag cc                                                          12

<210> SEQ ID NO 73
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 73
cccgaattcg cc                                                          12

<210> SEQ ID NO 74
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 74
ccgttgtttc cg                                                          12

<210> SEQ ID NO 75
<211> LENGTH: 28
<212> TYPE: DNA
<213> ORGANISM: Artificial Sequence
<220> FEATURE:
<221> NAME/KEY: misc_binding
<222> LOCATION: (1)...(28)
<223> OTHER INFORMATION: synthesized test oligonucleotide for binding
      studies

<400> SEQUENCE: 75
caacgatagc cgatgttagg cagctcac                                         28

<210> SEQ ID NO 76
<211> LENGTH: 21
<212> TYPE: DNA
<213> ORGANISM: Artificial Sequence
<220> FEATURE:
<221> NAME/KEY: misc_binding
<222> LOCATION: (1)...(21)
<223> OTHER INFORMATION: synthesized test oligonucleotide for binding
      studies

<400> SEQUENCE: 76
gcctaacatc ggctatcgtt g                                                21

<210> SEQ ID NO 77
<211> LENGTH: 28
<212> TYPE: DNA
<213> ORGANISM: Artificial Sequence
<220> FEATURE:
<221> NAME/KEY: misc_binding
<222> LOCATION: (1)...(28)
<223> OTHER INFORMATION: synthesized test oligonucletoide for binding
      studies

<400> SEQUENCE: 77
```

```
gtgagctgcc taacatcggc tatcgttg                                              28

<210> SEQ ID NO 78
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 78
caaaaatttt tc                                                                12

<210> SEQ ID NO 79
<211> LENGTH: 12
<212> TYPE: DNA
<213> ORGANISM: Artificial Sequence
<220> FEATURE:
<221> NAME/KEY: misc_binding
<222> LOCATION: (1)...(12)
<223> OTHER INFORMATION: synthesized test oligonucleotide for binding
      studies

<400> SEQUENCE: 79
cccgcgcgcg cc                                                                12

<210> SEQ ID NO 80
<211> LENGTH: 12
<212> TYPE: DNA
<213> ORGANISM: Artificial Sequence
<220> FEATURE:
<223> OTHER INFORMATION: oligonucleotide
<221> NAME/KEY: misc_feature
<222> LOCATION: (4)...(4)
<223> OTHER INFORMATION: n=a, t, c, or g
<221> NAME/KEY: misc_feature
<222> LOCATION: (9)...(9)
<223> OTHER INFORMATION: n=a, t, c, or g

<400> SEQUENCE: 80
cccnaattng cc                                                                12
```

NUCLEIC ACID LIGAND INTERACTION ASSAYS

This application CIP U.S. application Ser. No. 09/151,890, filed Sep. 11, 1998, which is hereby incorporated by reference in its entirety.

FIELD OF THE INVENTION

The invention is directed to the determination of relative binding affinities of various ligands to various nucleic acid sequences, particularly double stranded nucleic acid sequences, and in particular to the determination of binding specificities and base pair determinants of particular ligands via a competitive binding assay.

REFERENCES

Brophy, G. P. et al., U.S. Pat. No. 5,789,179 (1998).
Campbell, A. K., *Chemiluminescence: Principles and Applications in Biology and Medicine*; VCH, Ellis Horwood Ltd.: New York, 1988.
Cook, N. D., U.S. Pat. No. 5,665,562 (1997).
Haugland, R. P. (1996) *Handbook of Fluorescent Probes and Research Chemicals* (Spenze, M. T. Z., ed.) Molecular Probes, Eugene, Oreg.
Nieman, T., "Chemiluminescence: Techniques, Liquid-Phase Chemiluminescence", in *Encyclopedia of Analytical Science*, pp 613–621; Academic Press; Orlando, Fla., 1995.
Cantor, C. R., "Lighting Up Hybridization", *Nature Biotechnology* 14:264 (1996).
Chen, Q., Shafer, R. H., and Kuntz, I. D., *Biochemistry* 36:11402–7 (1997).
Hart, H., U.S. Pat. Nos. 4,271,139 (1978) and 4,382,074 (1983).
Morrison, L. E. and Stols, L. M., "Sensitive Fluorescence-Based Thermodynamic and Kinetic Measurements of DNA Hybridization in Solution", *Biochemistry* 32: 3095–3104 (1993).
Morrison, L. E., Halder, T. C., and Stols, L. M., "Solution Phase Detection of Polynucleotides Using Interacting Fluorescent Labels and Competitive Hybridization", *Anal. Biochem.* 183:231–244 (1989).
Saenger, W., in *Principles of Nucleic Acid Structure* (Cantor, C. R., ed.), Springer-Verlag, New York, 1984.
Tyagi, S. and Kramer, F. R., "Molecular Beacons: Probes that Fluoresce upon Hybridization", *Nature Biotech.* 14:303–306 (1996).
Tyagi, S., Bratu, D. P., and Kramer, F. R., "Multicolor Molecular Beacons for Allele Discrimination", *Nature Biotech.* 16:49–53 (1998).
Wilson, W. D., Tanious, F. A., Fernandez-Saiz, M., and Rigl, C. T., "Evaluation of Drug-Nucleic Acid Interactions by Thermal Melting Curves" in *Methods in Molecular Biology*, Vol. 90: *Drug-DNA Interaction Protocols* (Fox, K. R. ed.), Humana Press, Totawa, N.J., pp. 219–240.

BACKGROUND OF THE INVENTION

The specific molecular recognition of nucleic acids is fundamental to essential processes in molecular biology, including replication, transcription and translation. It has been shown that, in the majority of cases, binding of ligands to double-stranded nucleic acids stabilizes the duplex, or helical, form of DNA or RNA. (See, for example, Wilson et al.) The current understanding of the interactions between DNA or RNA and bound ligands is largely based on information obtained via biochemical and biophysical methods such as chemical and nuclease footprinting, affinity probing, UV, CD, fluorescent, and NMR spectroscopy, calorimetry, gel electrophoresis, and x-ray crystallography.

In a typical application of DNA footprinting, for example, a labeled oligonucleotide is digested with a DNA nuclease to the extent necessary to create an average of one cut per chain, producing a series of fragments differing by one base pair in length. A similar operation is performed on the oligonucleotide having a bound ligand. The ligand protects the oligonucleotide, at and around its binding site, from nuclease activity, creating a characteristic pattern of "missing" fragments at this site on a polyacrylamide gel following electrophoresis. This method suffers from the disadvantages of being very time and labor intensive, and in revealing not necessarily the critical molecular determinants for the ligand binding, but rather the area of the oligonucleotide that is shielded by the bulk of the ligand.

The most widely used method for studying nucleic acid hybridization is thermal denaturation, or melting, of duplex nucleic acids. Ligand binding has also been studied using thermal denaturation, since binding of ligands to duplex DNA or RNA tends to stabilize the helix against melting. Techniques used to observe this change include UV, fluorescent, CD and NMR spectroscopy, electrophoresis, and calorimetry.

Certain disadvantages are inherent in ligand binding studies based on observation of duplex denaturation, or melting. The methods provide information about binding only at or near the $T_m$ of the system, rather than at standard (25° C.) or physiological (37° C.) temperatures. Because the presence of the ligand generally raises the $T_m$ of the duplex, it is necessary that the ligand, e.g. the drug, be stable at this higher temperature. In addition, these methods do not routinely provide information about the binding site of the ligand (see, for example, Chen et al., 1997; Wilson et al., 1997). Therefore, the need exists for assays which are sensitive, are rapidly and simply carried out, and provide precise binding site information.

SUMMARY OF THE INVENTION

In one aspect, the invention provides methods of determining the binding affinity of a ligand to an oligonucleotide sequence. The methods are particularly useful for determining relative binding affinities of various ligands to various oligonucleotide sequences, particularly double stranded oligonucleotide sequences. One such method, described herein as a "direct" assay, comprises the following steps:

(i) providing first and second oligonucleotides, which are effective to hybridize by Watson-Crick base pairing to form a duplex;

wherein the first oligonucleotide comprises a first group effective to produce a detectable signal, and the second oligonucleotide comprises a second group, such that in the presence of the second group the signal is detectably altered upon hybridization of the first and second oligonucleotides, and in the absence of the second group the signal would not be detectably altered upon such hybridization;

(ii) forming a mixture of the oligonucleotides under conditions such that, in the absence of the ligand, the oligonucleotides exist primarily in single-stranded form;

(iii) observing the signal from the mixture in the absence of the ligand;

(iv) adding the ligand to the mixture; and (v) observing the signal from the mixture in the presence of the ligand.

By carrying out steps (i)–(v) for each of a plurality of pairs of such first and second oligonucleotides, the relative binding affinity of the plurality of oligonucleotide pairs for the ligand may be determined. Similarly, by carrying out steps (iv)–(v) for each of a plurality of ligands, whereby the relative binding affinity of the plurality of ligands for the oligonucleotide pair may be determined.

The ligand is typically a metal ion, a small organic or inorganic molecule, a protein, or a multi-protein complex, as defined herein. Preferably, the ligand is added to the mixture in increasing concentrations, and in step (v) above, the signal is thus observed in the presence of increasing concentrations of the ligand. The mixture may be held at a substantially constant temperature, e.g. at or near room temperature, as the ligand is added.

With respect to the oligonucleotide pair, the first group above is preferably attached at the 5'-end or 3'-end of the first oligonucleotide, while the second group is attached at the 3'-end or 5'-end, respectively, of the second oligonucleotide. In various embodiments, the first and second groups may be, respectively: a radiation emitting group and a group effective to absorb the emitted radiation; a group comprising a scintillant, and a radioactive group; or, a chemiluminescent group, and a group which participates in a chemiluminescent reaction with the first group. In another embodiment, the first group is effective to produce a detectable signal, as recited above, and the second group is effective to alter the proximity of the oligonucleotide duplex to a source which is effective to stimulate or modulate the production of the signal from the first group, where this stimulation or modulation is proximity-dependent. For example, the second group may be a binding group effective to bind to a surface. In one embodiment, the first group is an electrochemiluminescent group; in this case, the surface is preferably a metallic surface to which a voltage may be applied, or a magnetic surface effective to adhere to such a metallic surface.

A further method provided by the invention, described herein as a "kinetic strand displacement" assay, comprises the following steps:

(i) A mixture is formed of a first oligonucleotide, comprising a first group effective to produce a detectable signal, and a second oligonucleotide, effective to hybridize with the first oligonucleotide by Watson-Crick base pairing to form a duplex, and comprising a second group, such that in the presence of the second group the signal is detectably altered upon hybridization of the first and second oligonucleotides, and in the absence of the second group the signal would not be detectably altered upon such hybridization, essentially as recited above. In this method, the first and second oligonucleotides differ in length, such that the duplex has an overhang region. The further steps of the method include:

(ii) forming a duplex of the oligonucleotides, (iii) adding an unlabeled displacement strand which is effective to displace one of the oligonucleotides from the duplex in the absence of the ligand;

(iv) observing the signal from the mixture in the absence of the ligand;

(v) adding the ligand to the mixture; and (vi) observing the signal from the mixture in the presence of the ligand.

By carrying out steps (i)–(vi) for each of a plurality of pairs of such first and second oligonucleotides, the relative binding affinity of the plurality of oligonucleotide pairs for the ligand may be determined. Similarly, by carrying out steps (v)–(vi) for each of a plurality of ligands, the relative binding affinity of the plurality of ligands for the oligonucleotide pair may be determined.

In this assay, the forming, adding and observing steps described above can be carried out at a substantially constant temperature, e.g. at or near room temperature. The overhang region (i.e. the difference in length between the first and second oligonucleotides) is typically about 4–20 nucleotides in length.

In a further embodiment of this method, the following steps may be added: (vii) adding a competitor oligonucleotide, and (viii) observing the effect of such adding on the signal. The competitor oligonucleotide is typically selected from a duplex DNA, a duplex RNA, a duplex DNA/RNA hybrid, and a single stranded oligonucleotide.

A further method provided by the invention, described herein as a "competitive" assay, comprises the following steps:

(i) providing first and second oligonucleotides, which are effective to hybridize by Watson-Crick base pairing to form a duplex;

wherein the first oligonucleotide comprises a first group effective to produce a detectable signal, and the second oligonucleotide comprises a second group, such that in the presence of the second group the signal is detectably altered upon hybridization of the first and second oligonucleotides, and in the absence of the second group the signal would not be detectably altered upon such hybridization, essentially as recited above;

(ii) forming an indicator duplex of the oligonucleotides, having bound thereto the ligand, which is effective to stabilize the duplex;

(iii) adding a competitor oligonucleotide, and (iv) observing the effect of such adding on the signal.

By carrying out steps (i)–(iv) for each of a plurality of competitor oligonucleotides, the relative binding affinities of the plurality of competitor oligonucleotides for the ligand may be determined.

In a preferred embodiment of the method, the indicator duplex is formed, in step (ii), under conditions such that, in the absence of the ligand, the first and second oligonucleotides would exist primarily in single-stranded form. With respect to the oligonucleotide pair (i.e. the first and second oligonucleotides), the first group above is preferably attached at the 5'-end or 3'-end of the first oligonucleotide, while the second group is attached at the 3'-end or 5'-end, respectively, of the second oligonucleotide. Various embodiments of the first and second groups are described above.

In another preferred embodiment, the competitor oligonucleotide is unlabeled. The competitor oligonucleotide is typically selected from a duplex DNA, a duplex RNA, a duplex DNA/RNA hybrid, and a single stranded oligonucleotide. Such a single stranded oligonucleotide may be one which is capable of folding into a double stranded secondary structure.

In all of the assays of the invention, the ligand is typically selected from a metal ion, a small organic or inorganic molecule, a protein, and a multi-protein complex, as defined herein. The ligand may also be an oligonucleotide. Preferred ligands include small molecule ligands, as defined herein, i.e. biologically or chemically synthesized organic or inorganic compounds which are generally less than about 10,000 molecular weight, and more commonly less than 1,000 molecular weight. Proteins and small organic molecules are particularly preferred. Such a molecule is preferably permeable to cells, and is usually not a polypeptide or a polynucleotide.

BRIEF DESCRIPTION OF THE DRAWINGS

FIG. 1A is a schematic illustrating the equilibrium between single stranded and duplex nucleic acids, and the shift towards the duplex form upon ligand binding, in a direct assay;

FIG. 1B illustrates the effect of increasing drug concentration on the fluorescent signal, for an assay as illustrated in FIG. 1A, for drugs having different binding affinities;

DETAILED DESCRIPTION OF THE DRAWINGS

I. Definitions

Figure 2:
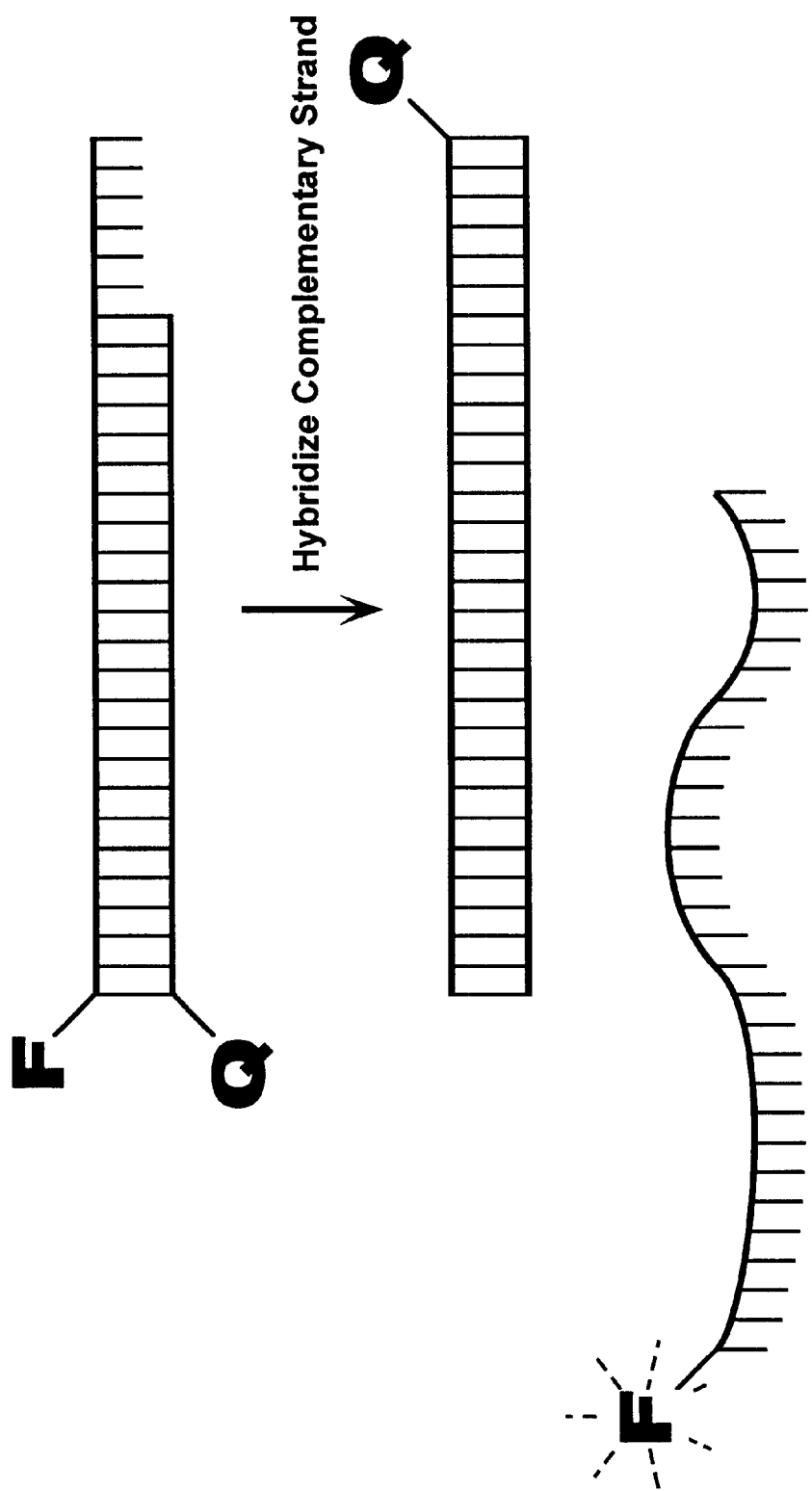
FIG. 2 is a schematic illustrating the displacement of a shorter, quenching strand from an F/Q indicator duplex by a longer, nonquenching strand, in a kinetic displacement assay.

The following terms, as used herein, have the following meanings unless indicated otherwise.

A "ligand" refers to any molecule or species which binds nucleic acids. Ligands may include a single metal ion (e.g. $Li^+$, $Na^+$, $Mg^2$, etc.), small molecule organic or inorganic compounds (e.g. polyamines, polyamides, polypeptides, or drugs), proteins, multi-protein complexes, or oligonucleotides.

"Binding," as used herein, generally refers to noncovalent association of a ligand, such as a protein or small molecule, with a nucleic acid molecule.

A "small molecule", as the term is used herein, refers to a biologically or chemically synthesized organic or inorganic compound that is generally less than about 10,000 molecular weight, and most commonly less than 1,000 molecular weight. A small molecule is preferably permeable to cells, and is usually not a polypeptide or a polynucleotide.

A "polypeptide", as used herein, refers to a polymer made up of a single chain of any or all of the 20 naturally occurring amino acids. The term "protein" may be synonymous with the term "polypeptide", or may refer, in addition, to a complex of two or more polypeptides. A "multi-protein complex" refers to a complex of proteins which is able to bind to a polynucleotide. The complex may be homomeric or heteromeric.

A "sequence-specific (or sequence-selective) nucleic acid binding ligand" is one which binds preferentially to one or more particular sequences or sequence motifs, or which is suspected to bind in such a manner. For example, such a ligand may show a preference for A/T-rich sequences over G/C-rich sequences, or it may show further discrimination, e.g. by distinguishing among various A/T motifs. A ligand may also bind selectively to a specific multibase sequence. Such ligands are contrasted to species which bind nonselectively to essentially any nucleic acid sequence, e.g. by simple electrostatic attraction.

An "oligonucleotide" or "polynucleotide", as used herein, includes naturally occurring DNA and RNA, and also includes a polymeric molecule having a backbone that supports nucleic acid bases capable of hydrogen bonding, in a sequence specific fashion, to naturally occurring nucleic acids. Such bases are typically inosine, adenosine, guanosine, cytosine, uracil and thymidine. The polymeric molecules may include polymers having backbone modifications such as methylphosphonate linkages.

A "duplex oligonucleotide sequence", as used herein, refers to a sequence of canonical double stranded RNA or DNA, typically 10 bp or longer, that exhibits Watson-Crick base-pairing along its length. The binding sites of a ligand may span, for example, 3–6 base pairs, 7–10 base pairs, or 10–20 base pairs of duplex oligonucleotide.

Two sequences which are "complementary" are able to form a duplex by exact one-to-one Watson-Crick base pairing between the bases in the two sequences, where adenine (A) base pairs with thymine (T), or uracil (U) in RNA, and cytosine (C) base pairs with guanine (G). Inosine (I) can base pair with cytosine, adenine, or uracil. A sequence which is complementary to a given sequence is referred to as its complement.

An "indicator pair" refers to first and second oligonucleotides, effective to form a duplex ("indicator duplex") by hybridization, where the first oligonucleotide has, typically at its 5' end, a group effective to produce a detectable signal, and the second oligonucleotide has, typically at its 3' end, a group effective to detectably alter this signal when the oligonucleotides form such a duplex. The first and second oligonucleotides are generally complementary. A signal is "detectably altered" when it is increased or decreased, or when the signal is produced where no signal was formerly present. In some embodiments of indicator pairs, the distinction between the "first" and "second" group may be somewhat arbitrary; e.g. for two groups which participate in a chemiluminescent reaction, as described further below.

A (second) group which is "effective to detectably alter" a signal may be a group which interacts directly with the signal-producing (first) group, such as a quenching group or a radioactive group. It may also be a group which does not necessarily interact directly with the signal-producing group, but which can alter the proximity of this group to a source (such as a source of voltage) which stimulates or modulates the signal from the first group. In such cases, the stimulation or modulation of the signal is dependent on the proximity of the first group to this source.

"Fractional saturating amount" is defined as the concentration at which a ligand binds to at least a certain defined fraction of available nucleic acid, which is typically duplex DNA or RNA. To achieve a fractional saturation of 50%, the required concentration of ligand is the thermodynamic binding constant $K_d$, if the concentration of RNA is significantly lower than the value of $K_d$. To achieve a fractional saturation of 90%, the required concentration is at least 10-fold greater than $K_d$. Thus, for a ligand having a $K_d$ of $1 \times 10^{-9}$ M, to achieve a fractional saturation of 90%, the concentration of the ligand required is at least $10 \times 10^{-9}$ M.

II. Ligand-Nucleic Acid Binding Assays: Assay Formats

A. Direct Binding Assay

In a direct binding assay, as provided herein, a mixture is formed of two oligonucleotides which are effective, under appropriate conditions of temperature, ion concentration, etc., to hybridize by Watson-Crick base pairing. Typically, the oligonucleotides are complementary, and are generally of the same length. The first oligonucleotide is labeled with a first group effective to produce a detectable signal, and the second oligonucleotide includes a second group which is effective to detectably alter this signal when the first and second sequences convert from single-stranded to double stranded conformation, i.e., upon sequence complementary hybridization. The second group may be one which is effective to alter the proximity of the bound duplex to a source which alters or modulates the detectable signal, typically by binding of the second group to a surface. Preferably, the first oligonucleotide is labeled at its 3' or 5' end, and the second oligonucleotide includes the second group at its 5' or 3' end, respectively.

An alternative arrangement (see Cantor, 1996) is that in which both first and second groups are on a single oligonucleotide which maintains the groups in proximity by assuming a "hairpin" conformation. When the oligonucleotide hybridizes with a second oligonucleotide, the groups become separated, and any proximity-dependent interaction between them is disrupted. Such a system could be applied to certain embodiments of the assays described herein.

The addition of a binding ligand to an oligonucleotide indicator pair, as defined above, will generally favor the formation of a duplex, bringing the interacting groups into proximity. This effect is illustrated for a fluorescence quenching system in FIG. 1A, where hybridization causes the fluorescent signal to decrease. In a preferred embodiment of the method, the ligand is a sequence-specific binding ligand, as defined above. Affinity of binding of a range of such ligands to a known sequence, or of a variety of sequences to a single ligand, can thus be evaluated based on the magnitude of this effect, as illustrated in FIG. 1B.

For maximum effectiveness of the assay, in terms of range of signal, the system is designed such that, in the absence of the ligand, the oligonucleotides exist primarily in single-stranded form. Variables that may be adjusted include the size and sequence of the oligonucleotides themselves and experimental conditions such as temperature, salt level, etc. In one embodiment, the assay is performed at a temperature that is somewhat higher than the $T_m$ of the duplex under the conditions (e.g. salt concentration) of the assay. The assay may be performed at or near room temperature but is not limited to any particular temperature. In a preferred embodiment, the assay is performed isothermally, that is, at a substantially constant temperature.

One advantage of the present assay, as opposed to conventional assays based on melting, is that it can be carried out at a substantially constant temperature, with the ligand added in increasing concentration. Preferably, the assays are performed at a temperature somewhat higher than the $T_m$ of the duplex under the assay conditions, so the oligonucleotides will be in single-stranded form at the outset of the assay; this gives the greatest range of signal, as the oligonucleotides convert from fully (or primarily) single-stranded to double-stranded. If desired, the length and composition of the oligonucleotides, and experimental conditions such as salt concentration, may be adjusted so that the assay can be carried out at or near room temperature. This is particularly applicable for shorter oligonucleotides. However, the assay is not limited to any particular temperature.

Because the assay is based on a shift in equilibrium, it may be used for transiently binding ligands. It is also suitable for very small ligands, such as metal ions. In contrast to labor-intensive methods such as DNA footprinting, the assay allows very rapid determination and comparison of ligand binding to RNA vs. DNA, and of G/C rich vs. A/T rich sequences. In this sense, it is well suited for high throughput screening methods, which can be performed in an automated mode using commercially available systems. In addition, the assay gives information pertaining to only the actual binding site of the ligand, even for large ligands, such as proteins. Previous methods such as DNA footprinting, as noted above, indicate only the region of the oligonucleotide masked by the protein, which may be much larger than the actual binding site.

For larger ligands, longer oligonucleotide sequences than those shown in Table I (see below) may be required for binding. In such cases, a fairly high temperature may be required to maintain these sequences in single-stranded form even in the absence of the ligand. In such cases, a kinetic displacement assay, performed at lower temperatures, preferably at ambient temperatures, may be preferred. Such assays are described further below.

Although the assay is preferably carried out in an isothermal mode, it may also be run in a more conventional melting-type format, where change in extent of hybridization is observed as a function of temperature. For example, in an assay designed to screen a large number of drugs for preference for RNA or DNA binding, arrays of wells are provided, each containing an RNA indicator pair labeled with a first dye, and a similar-sequence DNA indicator pair labeled with a second dye. The use of different fluorescent dyes permits simultaneous detection of different species. A test ligand is added to each well, and the wells are gradually heated. Ligands which bind either RNA or DNA (or both) will increase the $T_m$ of the respective indicator pairs, thus affecting the change in fluorescence with temperature. DNA vs. RNA binding is distinguished by the use of the two dyes, allowing detection at separate wavelengths. A similar format could be used to simultaneously screen a single drug for binding to an plurality of nucleic acid sequences.

B. Competitive Assay

Direct assays, as described above, are useful for first level screening of ligand-oligonucleotide binding, e.g. preference for DNA vs. RNA, or A/T vs. C/G rich sequences. In a "next-stage" assay, termed herein a competition or competitive assay, a binding oligonucleotide for a particular ligand, such as determined from direct assays, is used as an "indicator" for competitive studies, which give a further level of detail about ligand binding preferences. A competition experiment starts with first and second indicator oligonucleotides, as described above, containing, respectively, a first group effective to produce a detectable signal, and a second group effective to alter this signal. At the beginning of the assay, the ligand is bound to a duplex of the sequences. Again, experimental conditions of temperature, salt content, etc. are preferably adjusted such that, in the absence of the ligand, the oligonucleotides would exist primarily in single-stranded form. As noted above, the preferred temperature is somewhat higher than the $T_m$ of the duplex (in the absence of ligand) under the conditions of the assay. If desired, for the sake of convenience, conditions may be adjusted so that the assay can be carried out at or near room temperature.

As above, the first and second groups are preferably located at the 5' and 3' ends, respectively, of the first and second oligonucleotides. Various detection systems for the assays, based, for example, on fluorescence quenching or reemission, SPA, or chemiluminescence, are described below. For the purposes of the present description of the competitive assay, a fluorescence quenching indicator pair will be employed.

At the beginning of the assay, the indicator sequences form a duplex in the presence of the ligand, so fluorescence is at a minimum for the system. (When other detection systems are used, the signal observed will be that in which the first and second groups are in close proximity.) A "competitor" sequence, having no second (e.g. quenching) group, is then added, typically as a duplex with its complementary sequence. The competing sequence tends to remove the ligand from the indicator duplex at concentrations that become lower as the affinity of the competing sequence for the ligand becomes greater. Alternatively, the competing sequence removes the ligand more effectively at concentrations equimolar with the indicator duplex as the affinity of the competing sequence for the ligand becomes greater. As the ligand is removed, the indicator sequences denature to single-stranded form, quenching is no longer effective (in an F/Q system), and fluorescence increases.

The groups of "competitor" oligonucleotides shown in Tables III–VI (see below) provide a useful selection of sequence motifs for screening of a ligand which is believed to prefer A/T rich DNA sequences. Similar collections could be provided for C/G sequence motifs. As shown in the following examples, preferences among single-base variations in sequences 4–5 nucleotides in length, and the precise length of critical binding sequences, can be determined by this method.

Competitor oligonucleotides can include duplex DNA, duplex RNA, duplex RNA/DNA, and single stranded oligonucleotides. Because the assays of the invention are especially useful for evaluating ligand binding to double stranded nucleic acids, single stranded oligonucleotides which can fold into secondary structures are particulary contemplated. These secondary structures include hairpins, bulges, pseudoknots, adducted polynucleotides, four way junction polynucleotides, etc. However, any single stranded oligonucleotide can be used as a competitor oligonucleotide.

C. Kinetic Strand Displacement Assay

This version of the assay is based on the displacement of a shorter strand within an indicator duplex by a longer strand. Because this displacement generates a longer, more stable, duplex, it is favored by free energy considerations. Again, a duplex of first and second sequences, as described above, is used, but in this assay, the strands differ in length, thus creating a single stranded overhang region. In a fluorescence quenching assay format, for example, the "F" strand is generally longer than the "Q" strand. In most cases, a minimum overhang region of about 4–20 nucleotides is effective to initiate strand displacement. Because a longer region will increase the rate of displacement, and it is generally desirable in the assay to reduce the rate of displacement, so as to facilitate measurement, this length of 4–20 nucleotides is generally preferred. A length of 5–7 nucleotides is particularly preferred.

The first and second strands are allowed to form a duplex in the absence of the ligand. In the present example, the "F" and "Q" groups are thus in proximity, giving a minimum level (when Q is a quenching group) of fluorescence. The displacing strand is added, and the rate of displacement, as indicated by an increase (or other change) in fluorescence over time, is observed (see FIG. 2). The experiment is then repeated in the presence of increasing amounts of ligand. A strongly binding ligand will stabilize the initial duplex and thus slow the rate of displacement. It is also expected that a ligand binding closer to the overhang site will also have a greater effect on inhibiting displacement.

In a variation on this assay, an array of different RNA pairs is exposed to the test ligand, and then to a ds-RNA binding protein. In this case, the sequences which do not strongly bind the test ligand will have a more extensive protein coating, and thus will be less susceptible to displacement by a displacing RNA strand.

III. Detection Methods

A number of first and second group pairs may be used to provide a detection system. As defined above, the signal from the first group is "detectably altered" when it is increased or decreased, or when the signal is produced where no signal was formerly present. A (second) group which is "effective to detectably alter" the signal may be one which interacts directly with the signal-producing (first) group, such as a quenching group or a radioactive group. It may also be a group which does not necessarily interact directly with the signal-producing group, but which can alter the proximity of this group to a source (such as a source of voltage) which stimulates or modulates the signal from the first group. In such cases, the stimulation or modulation of the signal is dependent on the proximity of the first group to this source.

A. Fluorescence-Based Detection Systems

The first group may be a fluorescent group (F) such as fluorescein. Any of the many other fluorescent dyes known in the art and suitable for oligonucleotide labeling may also be used; see, for example, Haugland, 1996. These include rhodamine, Texas Red, lucifer yellow, and EDANS (5-((2-aminoethyl) amino)naphthalene-1-sulfonic acid, sodium salt), and the like. The second group (Q) is effective to detectably alter a fluorescent signal emitted from the fluorescent group when the first and second sequences hybridize to form a duplex. In one embodiment, the second group quenches the fluorescent signal, e.g. when the second group is Dabcyl™ (4-(4-dimethylaminophenylazo)benzoic acid), a known "universal" quencher. In this case, hybridization of the sequences results in a decrease in the observed level of fluorescence. Alternatively, the second group may be a second fluorescent group, effective to absorb the fluorescent radiation and re-emit it at a different wavelength, in a process known as FRET (fluorescence resonance energy transfer). The use of various fluorescence-based systems for detection of hybridization events, i.e. as probes in DNA assays, has been described, e.g. by Morrison et al., 1989, 1993; and Tyagi et al., 1996, 1998.

B. SPA Detection

In another embodiment, the first group is a scintillant, and the second group is a radioactive group. Such a system is used in the technique known as scintillation proximity assay (SPA), described in U.S. Pat. Nos. 4,382,074 and 4,271,139, which are hereby incorporated by reference in their entirety and for all purposes. Use of this technique in biological assays is also described in U.S. Pat. Nos. 5,789,179 and 5,665,562, also incorporated by reference. In this assay format, the signal observed is dependent upon the proximity of a labeled molecule, bound to special scintillating beads, to weak β-emitting (i.e. radiolabeled) compounds. When a radioactive atom decays, it releases sub-atomic particles, such as electrons. The distance these particles will travel through an aqueous medium is limited and is dependent on the nature of the radioactive atoms. If a radioactive atom such as $^{33}$P is in proximity to an SPA bead, which contains scintillant, electrons can reach the beads and stimulate the scintillant to emit light. However, if the radioactive atom is distant from the beads, the electrons do not reach the scintillant, and no light is emitted.

This technology can be applied to studies of ligand binding as disclosed herein. Example 13, below, describes the use of the assay in a high throughput screening method, using the SPA detection system. In this example, the first oligonucleotide is labeled with biotin, and is then tightly bound to streptavidin-coated SPA beads via the strong biotin/streptavidin interaction. These beads are impregnated with scintillant. The second oligonucleotide is labeled with a weak β-emitter, such as $^3$H or $^{33}$P. The radioactive second oligonucleotide is mixed with a solution of the beads under conditions at which the first and second oligonucleotides exist primarily as single strands, as described above. The signal will thus be low, as the oligonucleotides are non-hybridized. When ligand is added, the duplex form is stabilized, and the increased proximity of the radioactive isotope (e.g., $^3$H, $^{33}$P) in the second oligonucleotide causes the bead to which the first oligonucleotide is bound to scintillate. A signal thus indicates the presence of an effective binding ligand molecule; test sequences giving higher signals indicate the relative preference for different sequences.

One advantage of the SPA detection method over fluorescence quenching is the ability to use lower DNA concentrations; a typical SPA assay uses 0.5 nM DNA, while the fluorescent assay uses 25 nM DNA. This feature is especially useful for assaying more strongly binding ligands, as it is preferred in this assay to maintain the concentration of the nucleic acid below the $K_d$ value for its interaction with the ligand.

C. Chemiluminescence Detection

In another embodiment, one of the first and second groups is a chemiluminescent group, and the two groups participate in a chemiluminescent reaction; light is thereby emitted when the reaction takes place. Many such reactions are known in the art. (See, for example, Campbell, 1988; Nieman, 1995.) Useful liquid-phase chemiluminescent reactions, often used in detection systems, include the oxidation of luciferin, catalyzed by luciferase, and the oxidation of lucigenin to N-methylacridone in the presence of base and an Fe(II) catalyst. Luminol (5-amino-2,3-dihydro-1,4-phthalazinedione) also reacts with oxidants such as $H_2O_2$ in the presence of base and a copper(II) or iron(III) catalyst to produce an excited state product (3-aminophthalate, 3-APA) which gives off light at approximately 425 nm.

D. Electrochemiluminescence (ECL) Detection

A detection system based on electrochemiluminescence (ECL) technology may also be used for detection in the assays described herein. In this system, an electrochemiluminescent group, such as a ruthenium metal chelate, is linked to one nucleic acid strand, and produces a chemiluminescent signal in response to an applied voltage. Such systems, used for detection of hybridized DNA and in other assays, are described in a series of patents to Igen International, Inc., including U.S. Pat. Nos. 10 5,705,402, 5,635,347, and 5,770,459, which are hereby incorporated by reference in their entirety and for all purposes. As described in these references, ruthenium is the preferred metal species, although other transition metals and rare earth metals are also disclosed. The ruthenium ion is preferably bound to the oligonucleotide via a tris-(bipyridine) chelate. In recommended procedures, the assay is conducted in an electrolytic medium, such as a phosphate buffer, and a reductant, preferably tripropylamine (TPA), is present in the assay buffer in large molar excess. The reductant is consumed in the light-generating oxidation process, and in this process is effective to regenerate the reduced ruthenium ion.

Paramagnetic beads, functionalized with a binding reagent such as streptavidin, are added to the assay medium as a capture surface. The second hybridizing nucleic acid strand is provided with a complementary binding group, e.g. biotin, such that the second strand will become fixed to the magnetic beads. The beads are channeled into a flow cell and captured in a reaction chamber with a magnetized electrode. In accordance with the general assay methodology described herein, the first, electrochemiluminescent (e.g. Ru-labeled) oligonucleotide will form a duplex with the second, bead-bound oligonucleotide in the presence of a binding ligand, depending on the affinity of the ligand for the oligonucleotide sequence, and the concentration of the ligand. Material not affixed to the beads is washed away from the chamber. When voltage is applied across the chamber, the electrochemiluminescent group (e.g. ruthenium) on any hybridized nucleic acid emits light, which is detected. A significant advantage of this method is the stability of the ECL label, which, in the case of the ruthenium chelate, is reported to exceed a year.

E. Other Detection Methods

In principle, any method which can detect the transition from single-stranded to double stranded DNA could be used to study ligand binding using indicator oligonucleotides such as those shown in Table I, below. This could include methods which detect differences in properties, such as spectral characteristics or chromatographic mobility, between the single stranded and double stranded oligonucleotides. In such cases the oligonucleotides need not be labeled. For example, single-stranded oligonucleotides usually migrate differently from duplex nucleic acids during electrophoresis on polyacrylamide gels. This difference in migration could be used to observe the single-strand to duplex transition caused by the binding of ligands to nucleic acids. In such an assay, a mixture of the two oligonucleotides would be mixed, together with increasing concentrations of a test compound. One of the strands could be labeled with $^{32}$P in order to allow visualization after electrophoresis. Drug binding would be observed directly as a change in mobility of the oligonucleotideupon drug binding due to the stabilization of the duplex nucleic acid.

Liquid chromatographic and mass chromatographic methods which can distinguish single-stranded oligonucleotides from double-stranded oligonucleotides are also available. For example, the ligand dependent retention of the second strand of the indicator on a magnetic bead could be detected using mass spectrometry methods. These methods could also be applied to this ligand-binding assay.

The CD (circular dichroism) spectrum of nucleic acids is extremely sensitive to structural conformation, and single-stranded oligonucleotides have very different CD spectra from double-stranded oligos. This large spectral difference could be the basis of a detection scheme for studying ligand binding to nucleic acids. Fluorescence anisotropy could also be used to observe the ligand-induced hybridization of duplex nucleic acids.

Biosensor based instruments can detect very small changes associated with almost any binding event. This technology uses an evanescent field to measure minute changes in refractive index and thickness at the resonant mirror sensor surface. DNA/DNA hybridization can be detected using this method. As in SPA, one of the strands could be immobilized with biotin onto a surface, and the biosensor would then detect the drug-dependent binding of the second strand in the indicator duplex. The two strands could also be labeled with functional groups to cause a larger increase in signal upon hybridization.

IV. Demonstrations of Assays

A. Direct Binding Assay

A1. Fluorescence Quenching Examples

The specific examples described in this section employ fluorescence quenching as the detection system. In these examples, because conditions are adjusted to maintain the oligonucleotides in single-stranded form in the absence of the ligand, the assay starts with the system at a high or maximum level of fluorescence, and fluorescence generally decreases, depending on binding affinity, as the ligand is added.

Figure 3A:
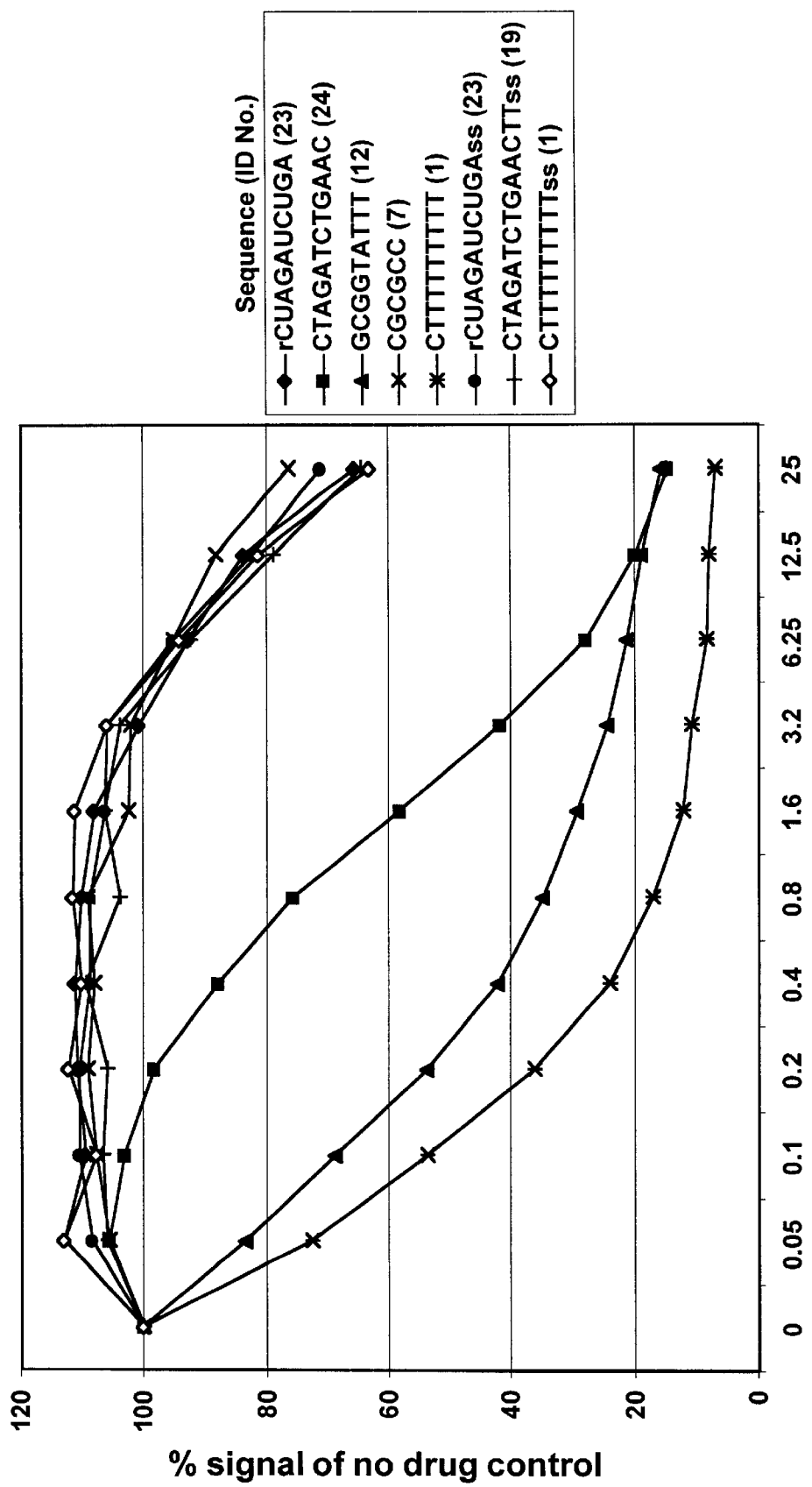
FIGS. 3A–3C show the decrease in fluorescence accompanying an increase in hybridization for a series of different-sequence DNA and RNA oligomers, in the presence of increasing amounts of netropsin (3A), bekanomycin (3B), and actinomycin D (3C)
Figure 3B:
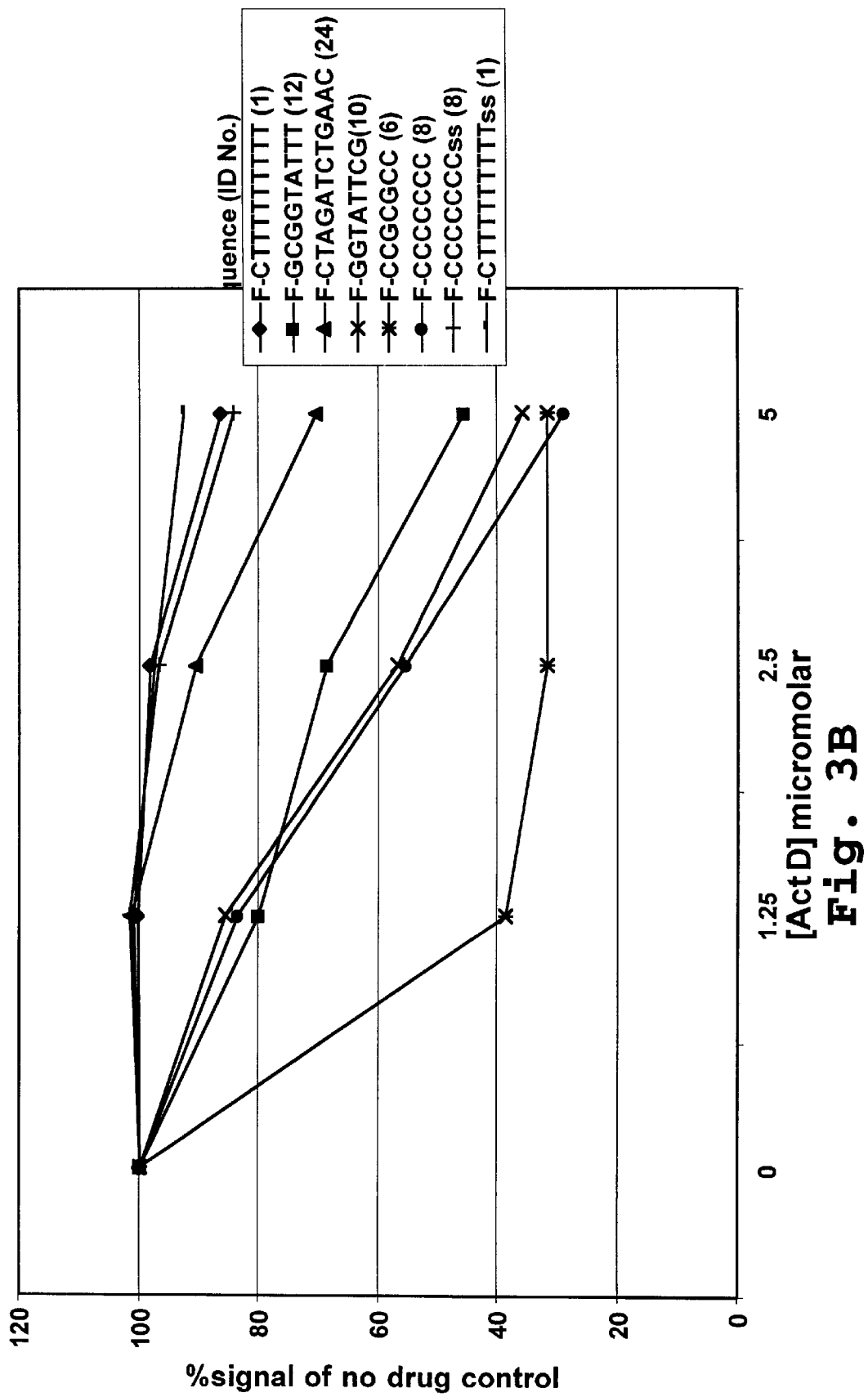
Figure 3C:
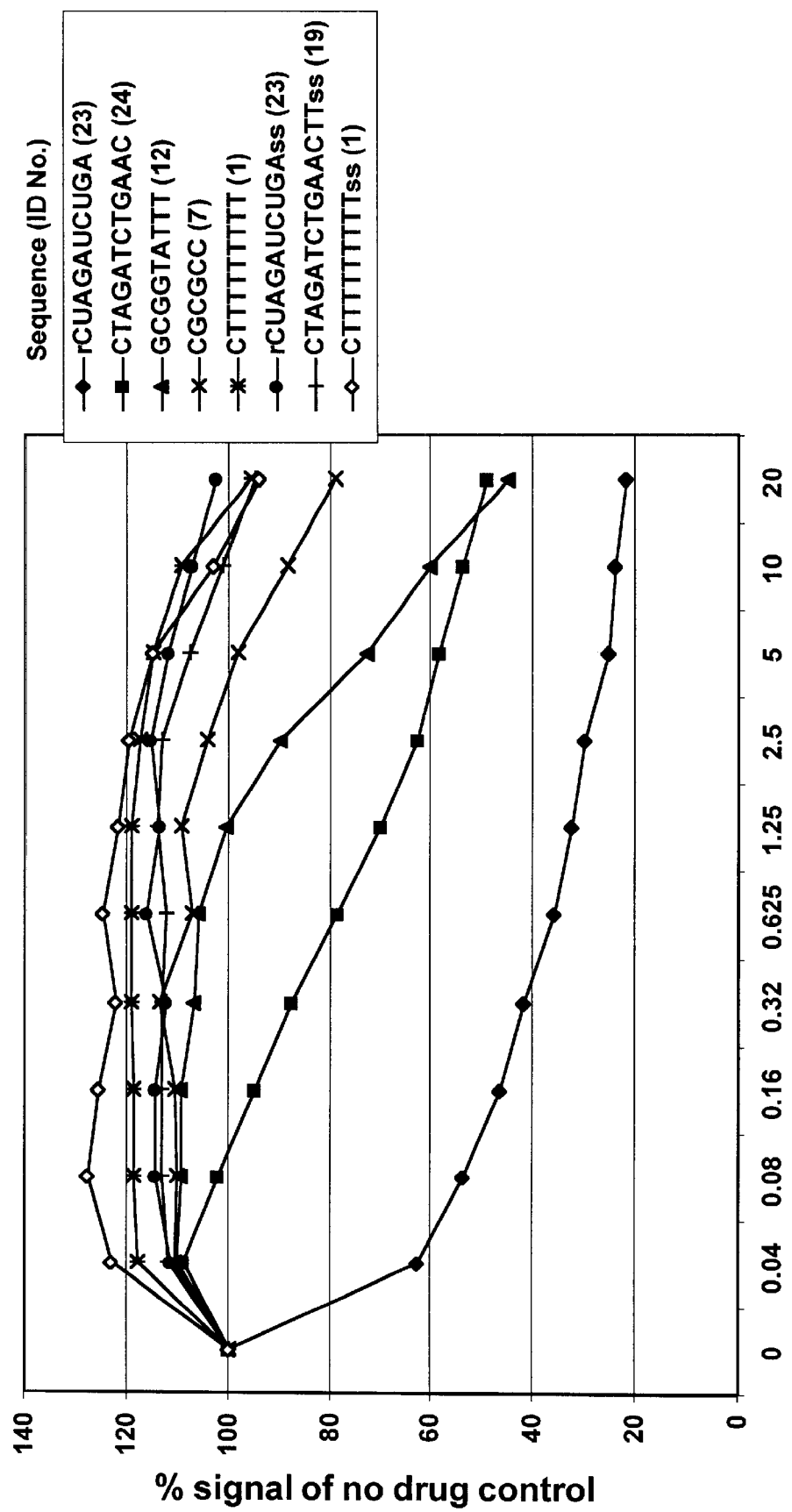

Binding curves representing the interaction of the drugs netropsin, bekanomycin, and actinomycin D with various oligos, in applications of the direct assay, are shown in FIGS. 3A–3C. The legends show the sequence of one strand of each F-Q indicator pair. These "indicator" oligonucleotides are also shown in Table I. The different types of oligos, as shown, allow side by side comparison of ligand binding with DNA sequences, RNA sequences, and A/T rich, G/C rich, or mixed sequences of both types. In Table III, most of the complementary strands are not shown. The complementary strands that are shown are indicated by (−) and are written in a 3'–5' orientation to show possible base pairing with the (+) strand.

TABLE I

Indicator Oligonucleotides

| Seq. ID No. | Type | Sequence |
| --- | --- | --- |
| 1 | A/T rich DNA | 5'-CTTTTTTTTT-3' |
| 2 | A/T rich DNA | 5'-CTTTATTATTTT-3' |
| 3 | Mixed DNA | 5'-CTCTCTCTC-3' |
| 4 | Inosine containing (+) | 5'-CCIICCIICC-3' |
| 5 | Inosine containing (−) | 3'-GGCCIICCGG-5' |
| 6 | G/C rich DNA | 5'-CCGCGCC-3' |

TABLE I-continued

Indicator Oligonucleotides

| Seq. ID No. | Type | Sequence |
| --- | --- | --- |
| 7 | G/C rich DNA | 5'-CGCGCG-3' |
| 8 | G/C rich DNA | 5'-CCCCCCC-3' |
| 9 | poly A/T DNA | 5'-GATATATATAG-3' |
| 10 | Mixed DNA | 5'-GGTATTCG-3' |
| 11 | Mixed DNA | 5'-GCGTATTT-3' |
| 12 | Mixed DNA | 5'-GCGGTATTT-3' |
| 13 | G/C rich DNA | 5'-CGCGCC-3' |
| 14 | Mixed RNA (+) | 5'-CUAGAUCUGAACUU-3' |
| 15 | Mixed RNA (−) | 3'-GAUCUAGACUUGAA-5' |
| 16 | Mixed RNA (−) | 3'-GAUCUAGACUUG-5' |
| 17 | Mixed RNA (−) | 3'-GAUCUAGACU-5' |
| 18 | Mixed RNA (−) | 3'-GAUCUAGAC-5' |
| 19 | Mixed DNA (+) | 5'-CTAGATCTGAACTT-3' |
| 20 | Mixed DNA (−) | 3'-GATCTAGACTTGAA-5' |
| 21 | Mixed DNA (−) | 3'-GATCTAGACTTG-5' |
| 22 | Mixed DNA (−) | 3'-GATCTAGACT-5' |
| 23 | Mixed RNA | 5'-CUAGAUCUGA-3' |
| 24 | Mixed DNA | 5'-CTAGATCTGAAC-3' |

In the Figure legends, RNA oligonucleotides are denoted by an "r" at the beginning of the sequence, and single stranded controls by "ss" at the end of the sequence. These single stranded sequence, are used alone in control experiments, which thus employ only an "F" strand and no complementary quenching strand. Any quenching of fluorescence that is not due to hybridization can thus be acounted for. Maximum quenching expected on complete hybridization of these oligonucleotides is 85–90%; therefore some signal remains after complete hybridization. The signal is plotted so that it is normalized to the control signal in the absence of ligand.

Netropsin has been shown in previous studies to bind preferentially to A/T rich regions of DNA. FIG. 3A shows the effect of adding increasing amounts of netropsin to mixtures of selected F/Q indicator oligonucleotide pairs, whose sequences are given in Table I. The sequence of the "F" strand of each pair is given in the figure legend, along with three single stranded controls, as indicated. From the data shown in FIG. 3A, it can be seen that netropsin strongly prefers the sequence 5'-CTTTTTTTTT-3' (SEQ ID NO: 1). Netropsin also binds well to the sequence 5'-GCGGTATTT-3' (SEQ ID NO: 12), which is a useful "indicator" probe (as discussed below), having both C/G and A/T rich sequences. The drug does not bind well to the G/C rich sequence 5'-CGCGCC-3' (SEQ ID NO: 7) or to RNA (5'-rCUAGAUCUGA-3'; SEQ ID NO: 23); for these oligos, the change in fluorescence was similar to that seen for the single-stranded controls.

FIGS. 3B and 3C show similar experiments performed with actinomycin D, which is generally believed to prefer binding to C/G rich regions of DNA, and bekanomycin, an RNA binding drug. Again, the "F" strand of each indicator pair is shown in the legend, along with single stranded controls. As shown in FIG. 3B, actinomycin D shows binding only to the C/G containing sequences (SEQ ID NOS: 6, 8, and 12) at concentrations up to 5 $\mu$M. Bekanomycin shows a very strong preference for the double stranded RNA probe (SEQ ID NO: 23) over all of the other test oligonucleotides (FIG. 3C).

Figure 3D:
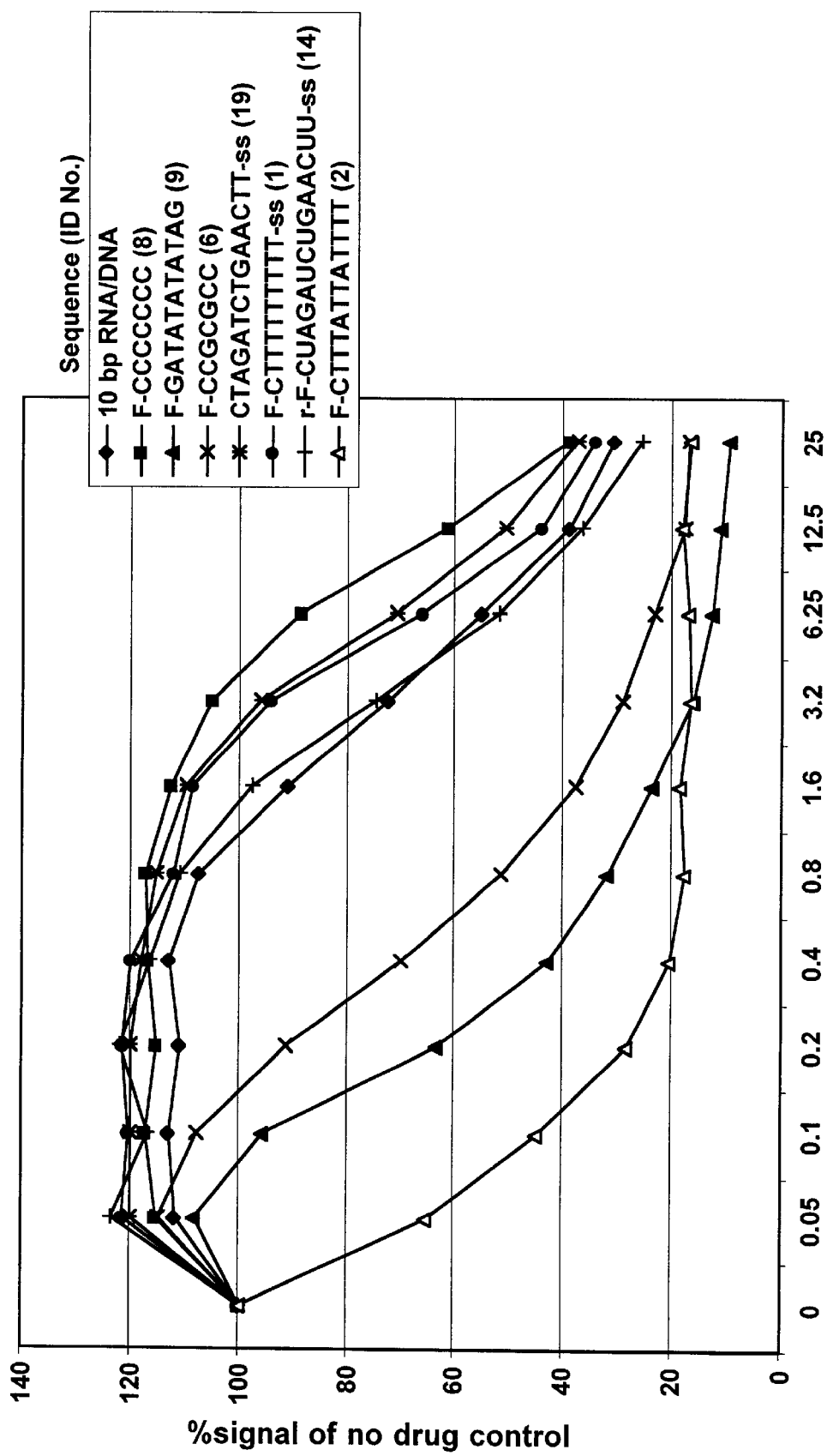
FIG. 3D shows the results of an experiment similar to that of FIG. 3A, carried out without the addition of a nonspecific binding agent (transfer RNA)

Interference from non-specific binding, based on electrostatic attraction, for example, may be reduced by addition of a competing non-specific binding species. For example, tRNA was added to the DNA binding experiment shown in FIGS. 3A and 3B. FIG. 3D shows the results of the study similar to that carried out for FIG. 3A, but without added tRNA. It can be seen that the presence of tRNA increased the distinction between the strongly binding sequence(s) and the remaining sequences. For RNA binding studies, non-specific binding compounds such as heparin or poly-dIdC may be used in place of tRNA.

A2. SPA (Scintillation Proximity) Detection Examples

The data in Table II compare raw signal counts from SPA assays using three different oligonucleotides and three concentrations (0, 100, and 500 nM) of the DNA binding drug distamycin. The oligonucleotides used were G/C-rich (CCGCGCC; SEQ ID NO: 6), A/T-rich (CTTTATTATTTT; SEQ ID NO: 2), or mixed sequence (GCGGTATTT; SEQ ID NO: 12) DNA duplexes. One strand of the duplex was synthesized with a 5'-biotin label, the other strand was labeled with $^{33}$P, as described in Example 13. As shown in the Table, the binding of distamycin preferentially stabilizes the A/T-rich duplex and the mixed duplex. These results are consistent with the behavior of these three oligonucleotides in the fluorescent assay format.

TABLE II

| | CPM | | |
|---|---|---|---|
| Oligo | No Drug | 100 nM Distamycin | 500 nM Distamycin |
| CCGCGCC (GC-rich) | | | |
| 10 mM Na+ | 577 | 699 | 744 |
| 50 mM Na+ | 842 | 889 | 666 |
| GCGGTATTT (mixed) | | | |
| 10 mM Na+ | 318 | 597 | 1951 |
| 50 mM Na+ | 261 | 868 | 2234 |
| CTTTATTATTTT (AT-rich) | | | |
| 10 mM Na+ | 244 | 2218 | 3332 |
| 50 mM Na+ | 399 | 2448 | 3352 |

Figure 4A:
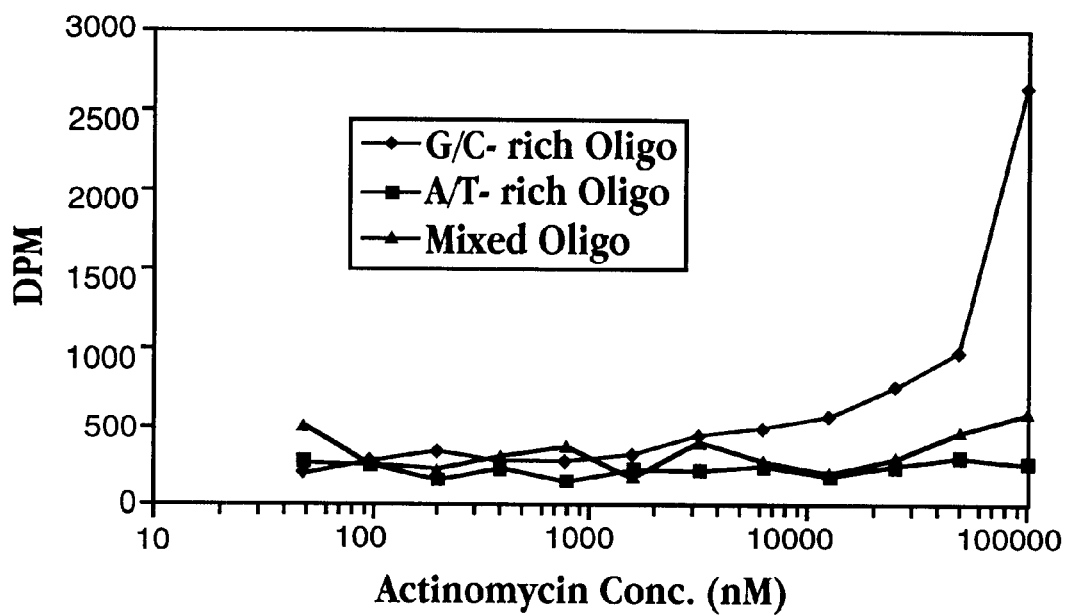
FIGS. 4A–E show the increase in the SPA scintillation counts accompanying an increase in hybridization of oligonucleotide indicator pairs labeled with $^{33}$P and biotin, respectively, for a series of different-sequence DNA oligomers, in the presence of increasing amounts of five known DNA-binding molecules.
Figure 4B:
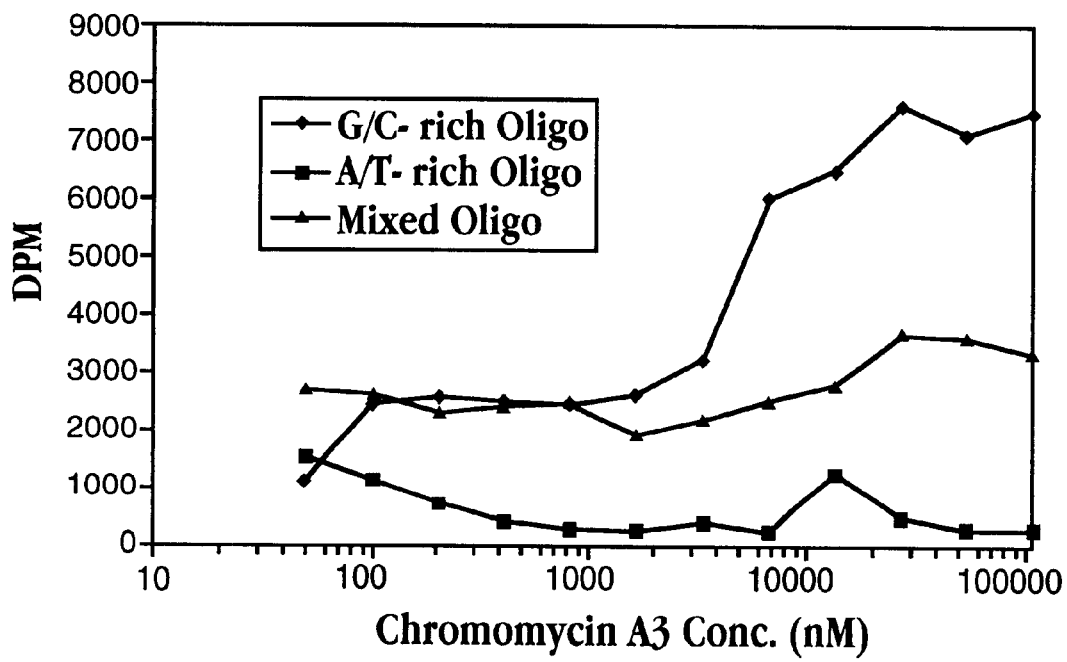
Figure 4C:
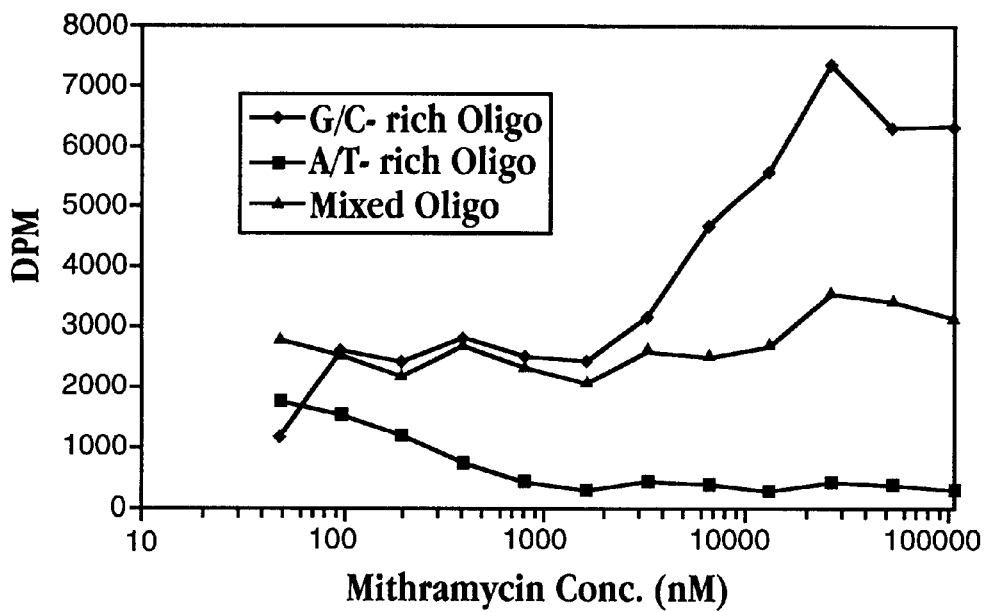
Figure 4D:
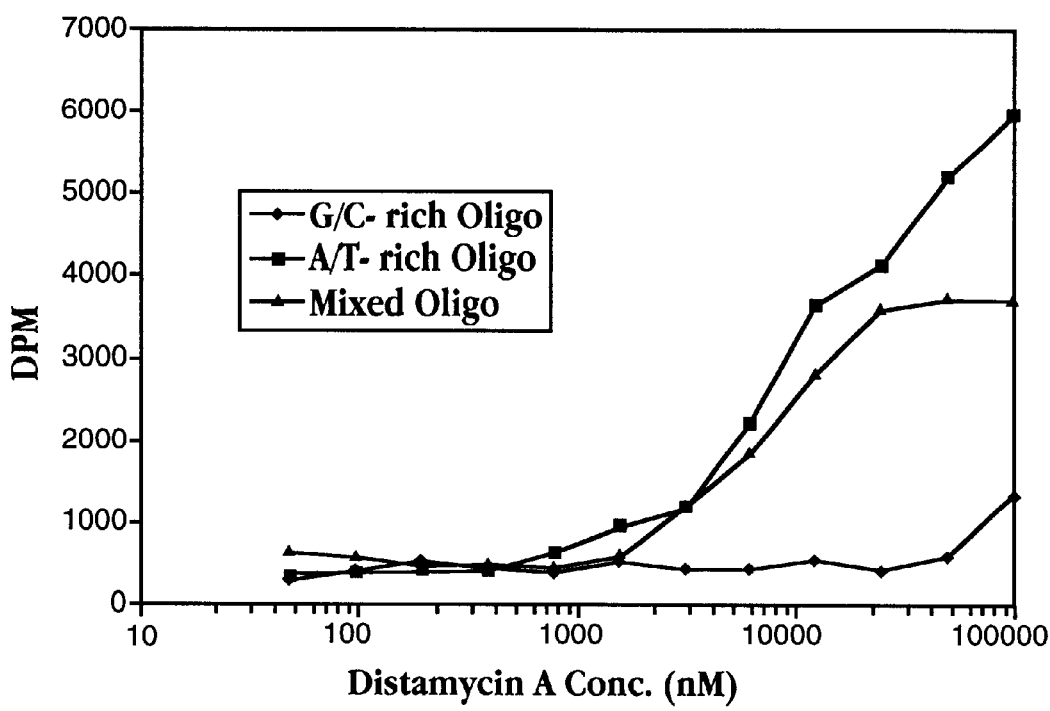
Figure 4E:
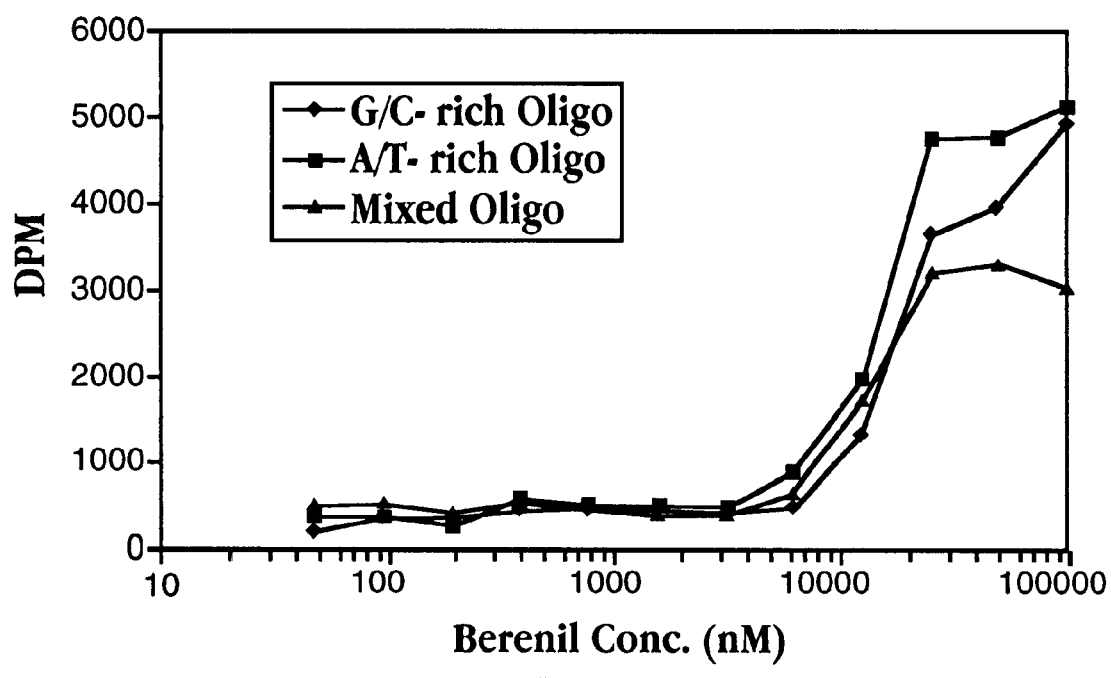

To produce the data shown in FIGS. 4A–E, each of five known DNA-binding molecules was tested for binding with an A/T rich oligonucleotide(5'-AAAATAATAAAG; complement of SEQ ID NO: 2), a G/C rich oligonucleotide (5'-GGCGCGG; complement of SEQ ID NO: 6), and a mixed sequence oligonucleotide (5'-GTTGCAGATC; SEQ ID NO: 80). Distamycin showed a preference for A/T-rich and mixed sequences (FIG. 4A); mithramycin, chromomycin A, and actinomycin D preferred GC-rich sequences (FIGS. 4B–D); and no strong preference was observed for berenil (FIG. 4E).

A3. ECL (Electrochemiluminescence) Detection Examples

The sensitivity and detection limit of the ECL detection method were first tested with a complementary oligonucleotide pair, the first strand labeled with a ruthenium tris(bipy) chelate 5' and the second with biotin 3'. An excess of paramagnetic strepavidinated beads was used to obtain the maximum signal independent of ligand mediated hybridization. Background was measured with a ruthenium-labeled ssDNA. In this system, signal to noise at ratio optimal DNA concentration was 160, and DNA concentrations as low as 1–2pM were detected above 2× background. In further experiments, background was measured by omitting the magnetic beads, the method recommended by Igen. Concentrations of 0.1 and 0.25 nM DNA were chosen as optimal for this detection method. This data indicates a 10-fold increase in sensitivity over SPA (scintillation proximity assay) detection.

Figure 5A:
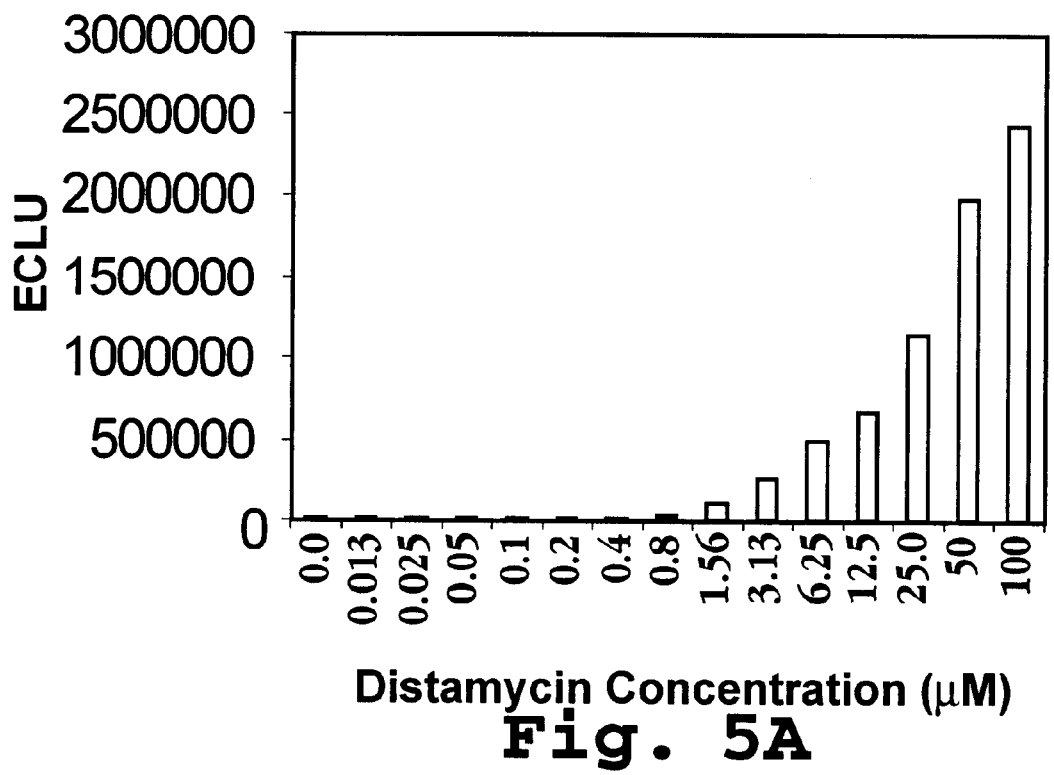
FIGS. 5A and 5B show the increase in the ECL signal upon adding increasing amounts of distamycin (FIG. 5A) and berenil (FIG. 5B) to a oligonucleotide indicator pair labeled with a ruthenium chelate and with biotin, respectively, as described below.
Figure 5B:
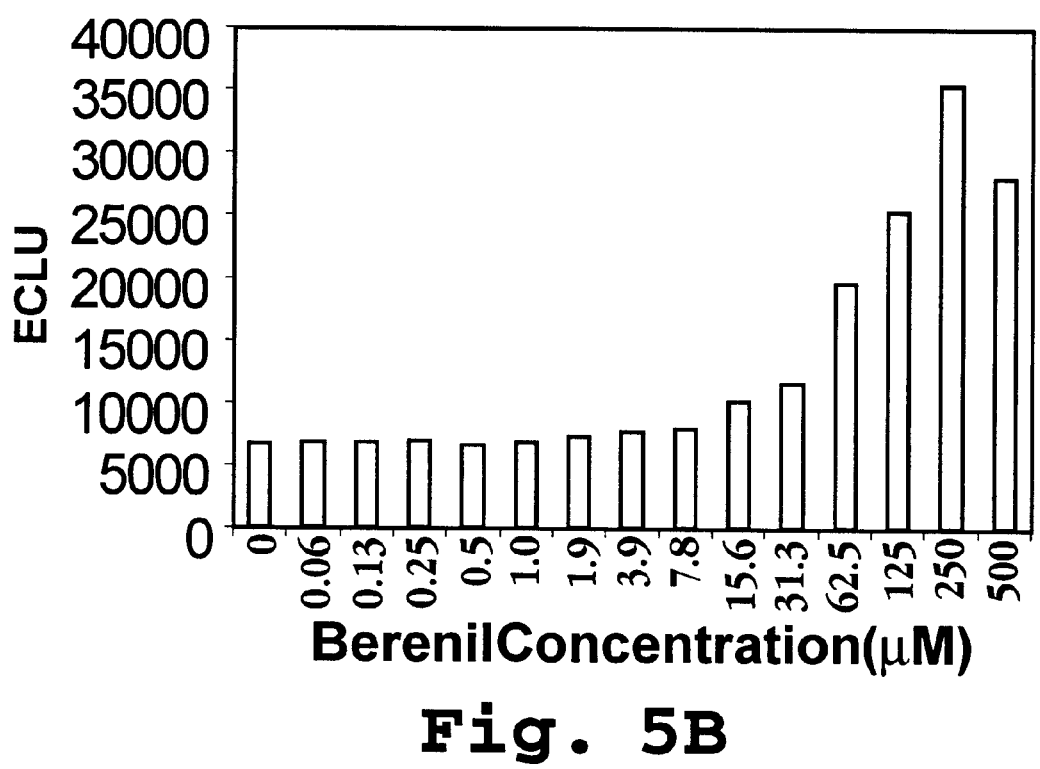

FIGS. 5A and 5B show the results of adding increasing amounts of distamycin (FIG. 5A) and berenil (FIG. 5B) to a oligonucleotide indicator pair (sequence 5'-GCGGTATTT-3'; SEQ ID NO: 12). The indicator pair was labeled with 5' ruthenium on one strand and 3' biotin on the complementary strand. Two fold dilutions of the drugs were added to the indicator pair and incubated for 30 min at r.t.; paramagnetic beads were then added to the mixture, at a final concentration of 0.0167 mg/ml, and incubated for 30 min at r.t. Any duplex DNA formed by ligand binding mediated hybridization were captured by the streptavidin coating on the beads, and the captured ruthenium was quantitated with the IGEN Origen™ analyzer, as described in Example 14.

B. Competitive Assay

B1. Fluorescence Quenching Examples

Figure 6:
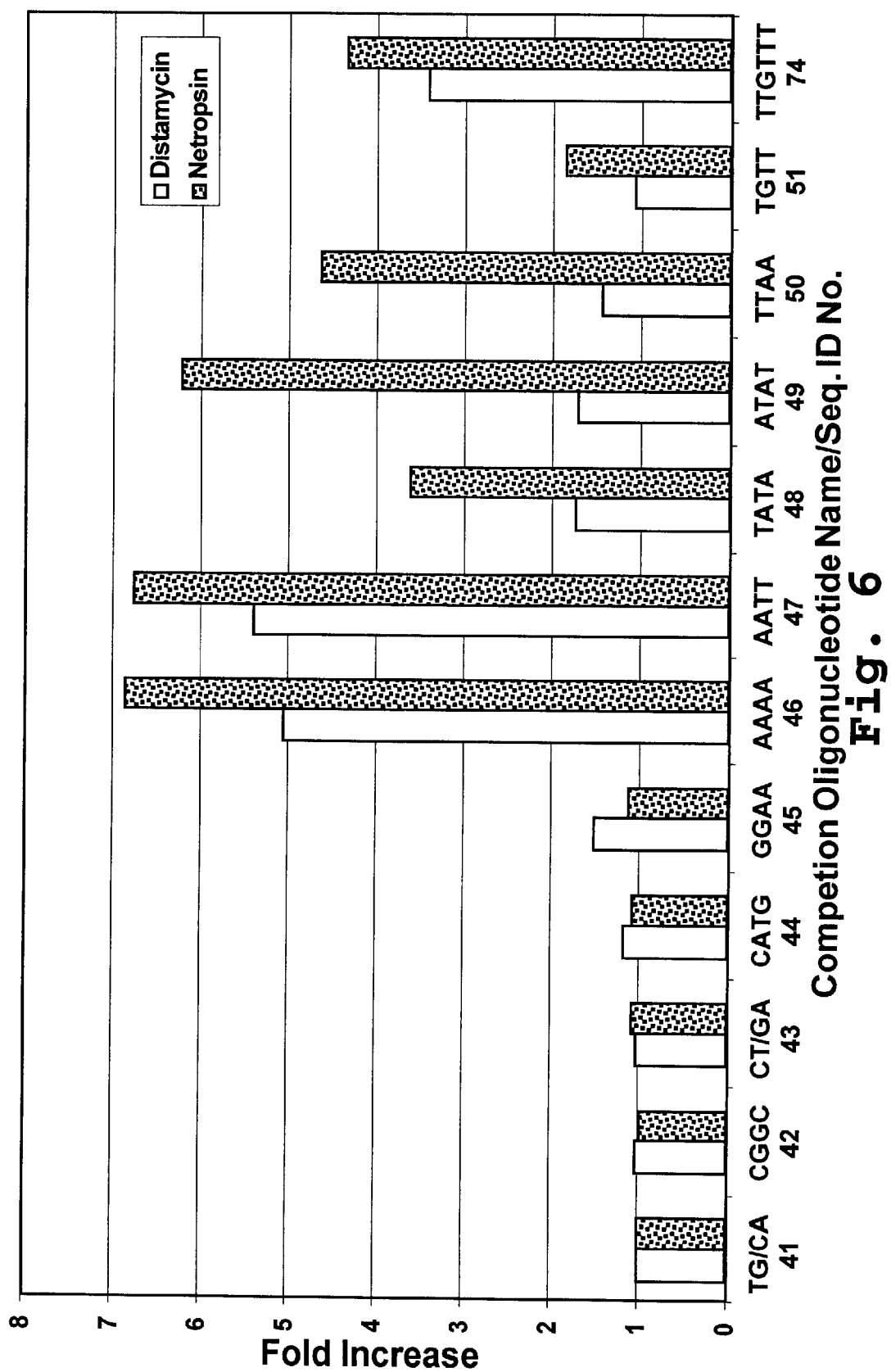
FIG. 6 shows the increase in fluorescence upon adding competitor oligonucleotides containing various sequence motifs to an F/Q "indicator" duplex having bound distamycin or netropsin, respectively, in a competitive assay.

Results of a typical competition assay are shown in FIG. 6, where the fluorescent signal of netropsin and distamycin bound to a duplex of an A/T rich "indicator" molecule (5'-CTTTATTATTTT-3'; SEQ ID NO: 2, and its complement) is compared to the signal in the presence of equal concentrations of different competitor oligos, whose sequences (SEQ ID NOs: 41–51 and 74) are listed in Table III. An increase in signal, as described above, indicates that the drug is binding the unlabeled competitor oligonucleotiderather than the indicator molecule, causing a shift in equilibrium back towards single-stranded indicator oligos.

TABLE III

| Sequences of Competitor Oligonucleotides | | |
|---|---|---|
| Seq. ID No. | Name | Sequence |
| Mixed Sequence Controls: | | |
| 41 complement | TG/CA | 5'-GTGTGTGTGTGTG-3' 3'-CACACACACACAC-5' |
| 42 | CGGC | 5'-CCCGGCCGGCCC-3' 3'-GGGCCGGCCGGG-5' |
| 43 | CT/AG | 5'-CTCTCTCTCTCTC-3' 3'-GAGAGAGAGAGAG-5' |
| 44 | CATG | 5'-CATGTCAGTCGA-3' 3'-GTACAGTCAGCT-5' |
| 45 | GGAA | 5'-GGAAGGAAGGAA-3' 3'-CCTTCCTTCCTT-5' |
| Four bp A + T sites: | | |
| 46 | AAAA | 5'-CCCGAAAACGCC-3' 3'-GGGCTTTTGCGG-5' |
| 47 | AATT | 5'-CCCGAATTCGCC-3' 3'-GGGCTTAAGCGG-5' |
| 48 | TATA | 5'-CCCGTATACGCC-3' 3'-GGGCATATGCGG-5' |
| 49 | ATAT | 5'-CCCGATATCGCC-3' 3'-GGGCTATAGCGG-5' |
| 50 | TTAA | 5'-CCCGTTAACGCC-3' 3'-GGGCAATTGCGG-5' |
| 51 | TGTT | 5'-CCCGTGTTCGCC-3' 3'-GGGCACAAGCGG-5' |
| 74 | TTGTTT | 5'-CCGTTGTTTCCG-3' 3'-GGCAACAAAGGC-5' |

The data in FIG. 6 show that A/T rich competitor sequences were more effective in removing ligand from the indicator duplex, causing an increase in fluorescence as the indicator duplex denatures. It is thus clear that netropsin and distamycin are relatively specific ligands that strongly prefer A/T rich DNA, consistent with the results shown in FIG. 3.

Figure 7:
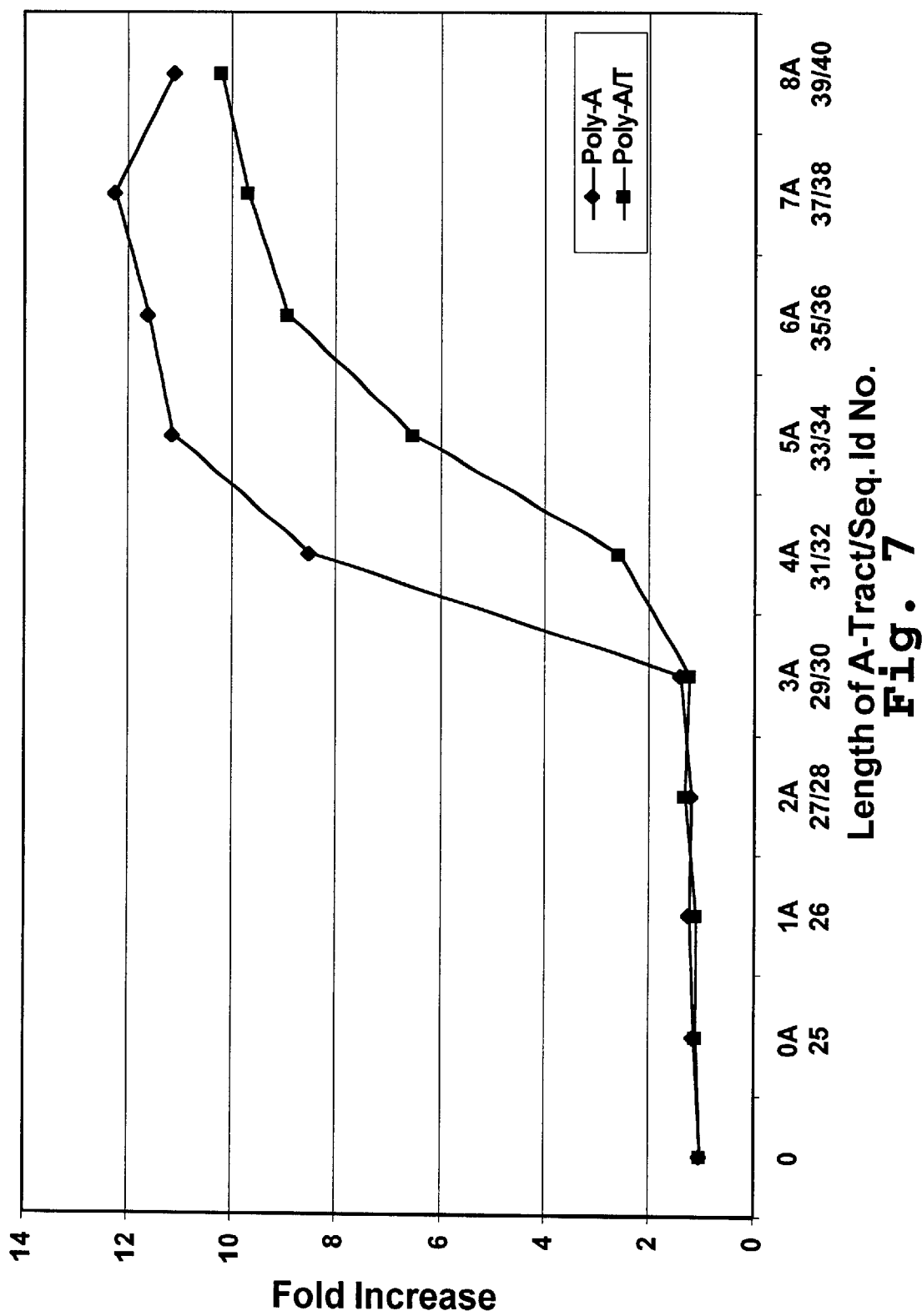
FIGS. 7 and 8 show the increase in fluorescence upon adding competitor oligonucleotides having different lengths of poly-A and poly-TA tracts to an F/Q indicator duplex having bound distamycin or netropsin, respectively.
Figure 8:
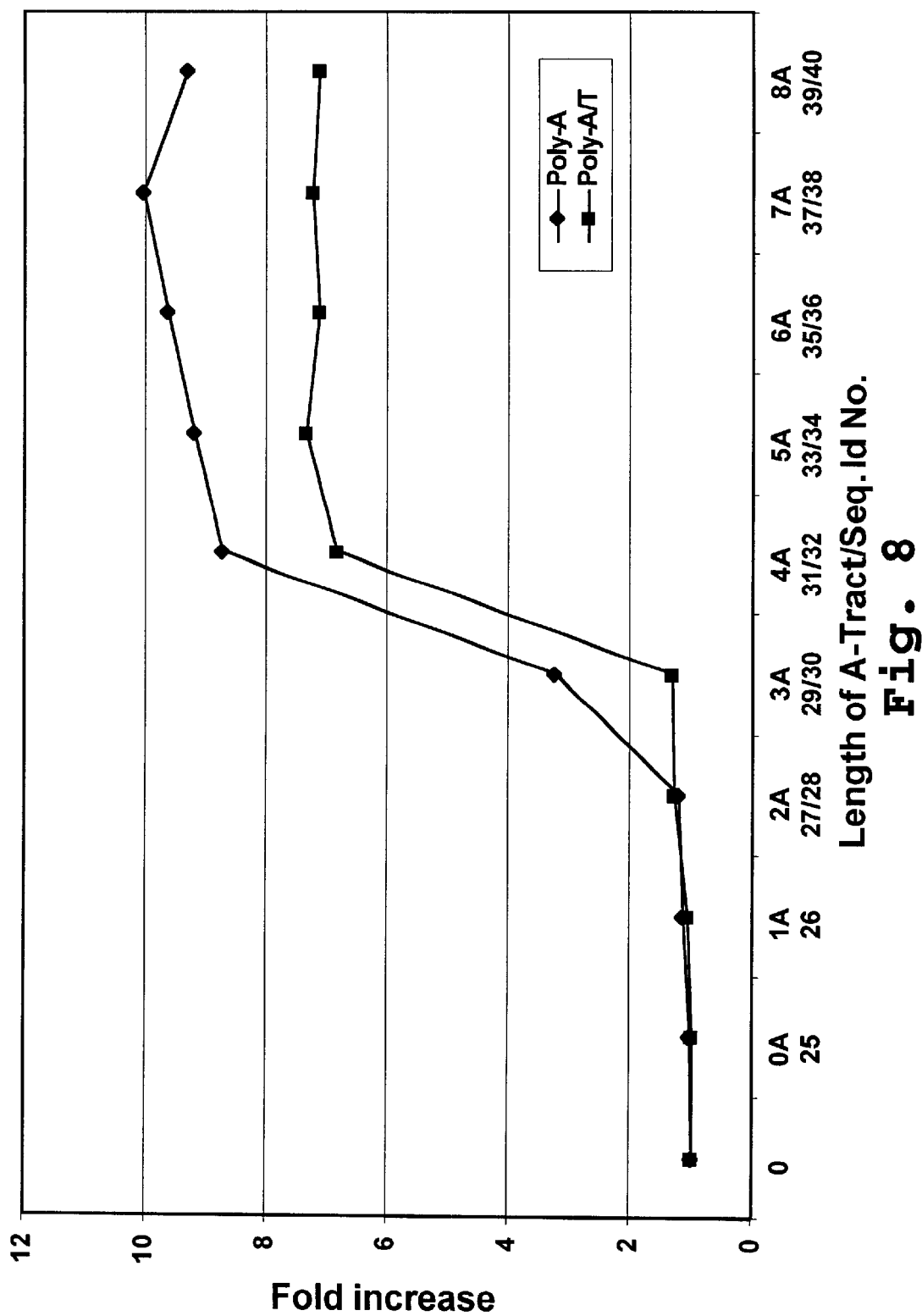

To further explicate the specificity of these drugs, i.e., to determine the preferred length of A/T rich binding determinants for each drug, a competition study was done using A-tracts of increasing length. Competitor oligonucleotides containing two different types of A-tracts, either homopolymer poly-A type or alternating poly-TA type, were used. These oligonucleotides are listed in Table IV (SEQ ID NOs: 25–40). The results of the study are shown in FIGS. 7 and 8. The data shows that both drugs bind relatively weakly to A-tracts of 3 or less, but binding sharply increases for 4 bp A-tracts, particularly in the case of poly-A. The results also show that for both drugs a slightly longer poly-TA tract is needed to compete for drug binding than the corresponding poly-A tract. This is consistent with the data shown in FIG. 6, indicating that these drugs, especially distamycin, strongly prefer binding to AAAA over TATA. In fact, for both drugs, the most favored sequences of those examined are those containing AAAA/TTTT and AATT (FIG. 6).

TABLE IV

Sequences of Competitor Oligonucleotides

| Seq. ID No. | Name | Poly-A | Poly-A/T |
|---|---|---|---|
| 25 complement | 0 A | 5'-CCCGGCCGGCCC-3' 3'-GGGCCGGCCGGG-5' | Same Oligo |
| 26 complement | 1 A | 5'-CCCGGACGGCCC-3' 3'-GGGCCTGCCGGG-5' | Same Oligo |
| 27, 28 complements | 2 A | 5'-CCCGGAACCGCC-3' 3'-GGGCCTTGGCGG-5' | 5'-CCCGGTACCGCC-3' 3'-GGGCCATGGCGG-5' |
| 29, 30 | 3 A | 5'-CCCGAAACCGCC-3' 3'-GGGCTTTGGCGG-5' | 5'-CCCGATACCGCC-3' 3'-GGGCTATGGCGG-5' |
| 31, 32 | 4 A | 5'-CCCGAAAAGCC-3' 3'-GGGCTTTTGCGG-5' | 5'-CCCGATATCGCC-3' 3'-GGGCTATAGCGG-5' |
| 33, 34 | 5 A | 5'-CCCAAAAACGCC-3' 3'-GGGTTTTTGCGG-5' | 5'-CCCTATATCGCC-3' 3'-GGGATATAGCGG-5' |
| 35, 36 | 6 A | 5'-CCCAAAAAAGCC-3' 3'-GGGTTTTTTCGG-5' | 5'-CCCTATATAGCC-3' 3'-GGGATATATCGG-5' |
| 37, 38 | 7 A | 5'-CCAAAAAAAGCC-3' 3'-GGTTTTTTTCGG-5' | 5'-CCATATATAGCC-3' 3'-GGTATATATCGG-5' |
| 39, 40 | 8 A | 5'-CCAAAAAAAACC-3' 3'-GGTTTTTTTTGG-5' | 5'-CCATATATATCC-3' 3'-GGTATATATAGG-5' |

The succeeding examples show the influence of the sequence determinants outside of these four based pair core elements on distamycin and netropsin binding. It was expected that, because distamycin had been shown to interact with more than 4 base pairs, sequences flanking the high affinity AATT site may be important. This was investigated using a set of competitor oligonucleotides containing all possible sequences in the arrangement 5'-XAATTY-3' (SEQ ID NOs 64–73; see Table V). Because AATT is a palindrome, there are ten unique combinations of this sequence.

TABLE V

Sequences of Competitor Oligonucleotides: 5'-XAATTY-3' Series
5'-CCCXAATTYGCC-3' (SEQ ID NO: 80)
3'-GGGYTTAAXCGG-5' (complement)

| Seq. ID No. | Name (XY/XY) | Sequence |
|---|---|---|
| 64 complement | CC/GG | 5'-CCCCAATTCGCC-3' 3'-GGGGTTAAGCGG-5' |
| 65 | CA/TG | 5'-CCCCAATTAGCC-3' 3'-GGGGTTAATCGG-5' |
| 66 | AG/CT | 5'-CCCAAATTGGCC-3' 3'-GGGTTTAACCGG-5' |
| 67 | CG | 5'-CCCCAATTGGCC-3' 3'-GGGGTTAACCGG-5' |
| 68 | AC/GT | 5'-CCCAAATTCGCC-3' 3'-GGGTTTAAGCGG-5' |
| 69 | AA/TT | 5'-CCCAAATTAGCC-3' 3'-GGGTTTAATCGG-5' |
| 70 | AT | 5'-CCCAAATTTGCC-3' 3'-GGGTTTAAACGG-5' |
| 71 | GA/TC | 5'-CCCGAATTAGCC-3' |

TABLE V-continued

Sequences of Competitor Oligonucleotides: 5'-XAATTY-3' Series
5'-CCCXAATTYGCC-3' (SEQ ID NO: 80)
3'-GGGYTTAAXCGG-5' (complement)

| Seq. ID No. | Name (XY/XY) | Sequence |
|---|---|---|
| | | 3'-GGGCTTAATCGG-5' |
| 72 | TA | 5'-CCCTAATTAGCC-3' 3'-GGGATTAATCGG-5' |
| 73 | GC | 5'-CCCGAATTCGCC-3' 3'-GGGCTTAAGCGG-5' |

Figure 9:
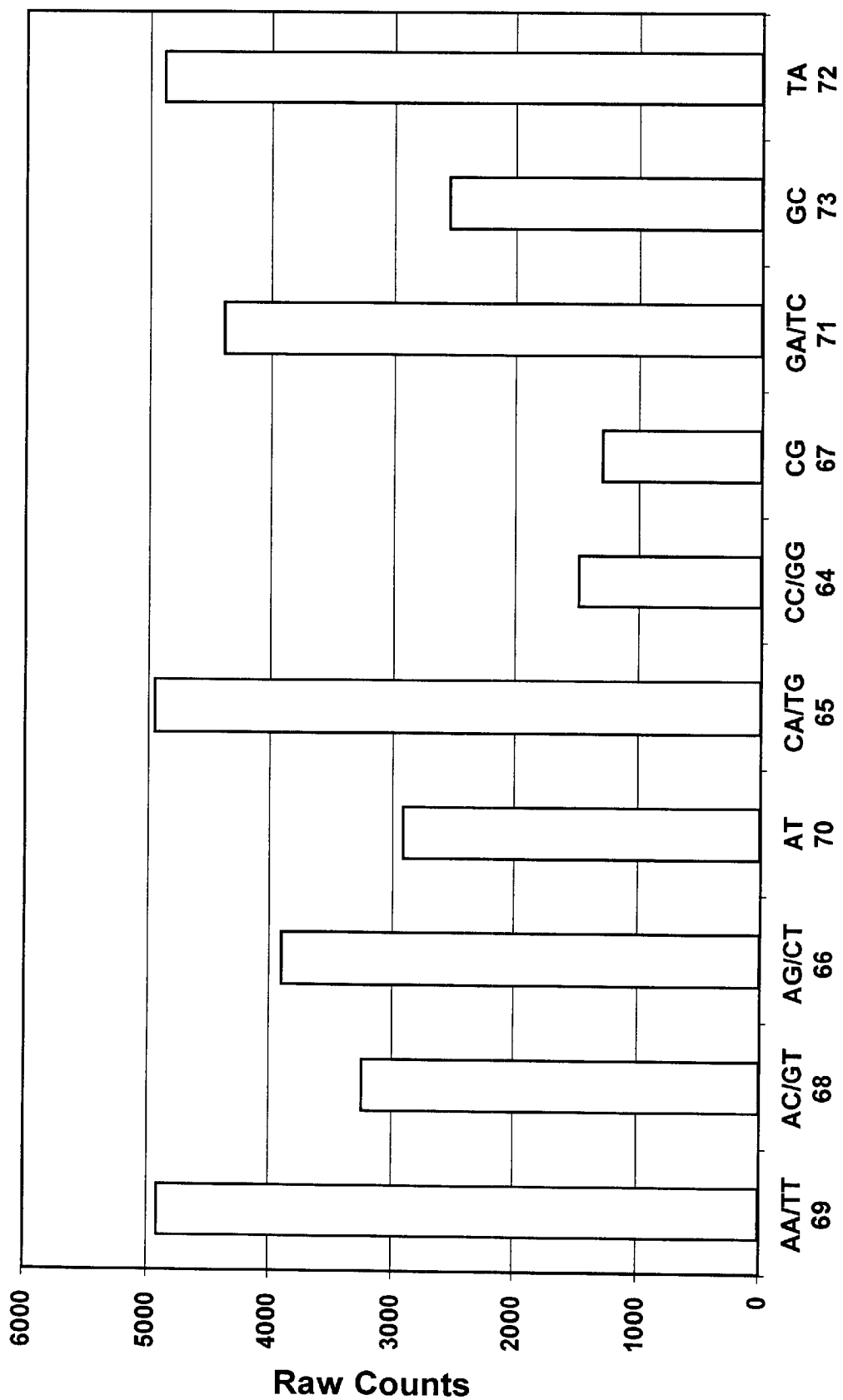
FIGS. 9 and 10 show the increase in fluorescence upon adding a series of competitor oligonucleotides, having different bases flanking an AATT sequence, to an F/Q indicator duplex having bound distamycin or netropsin, respectively.
Figure 10:
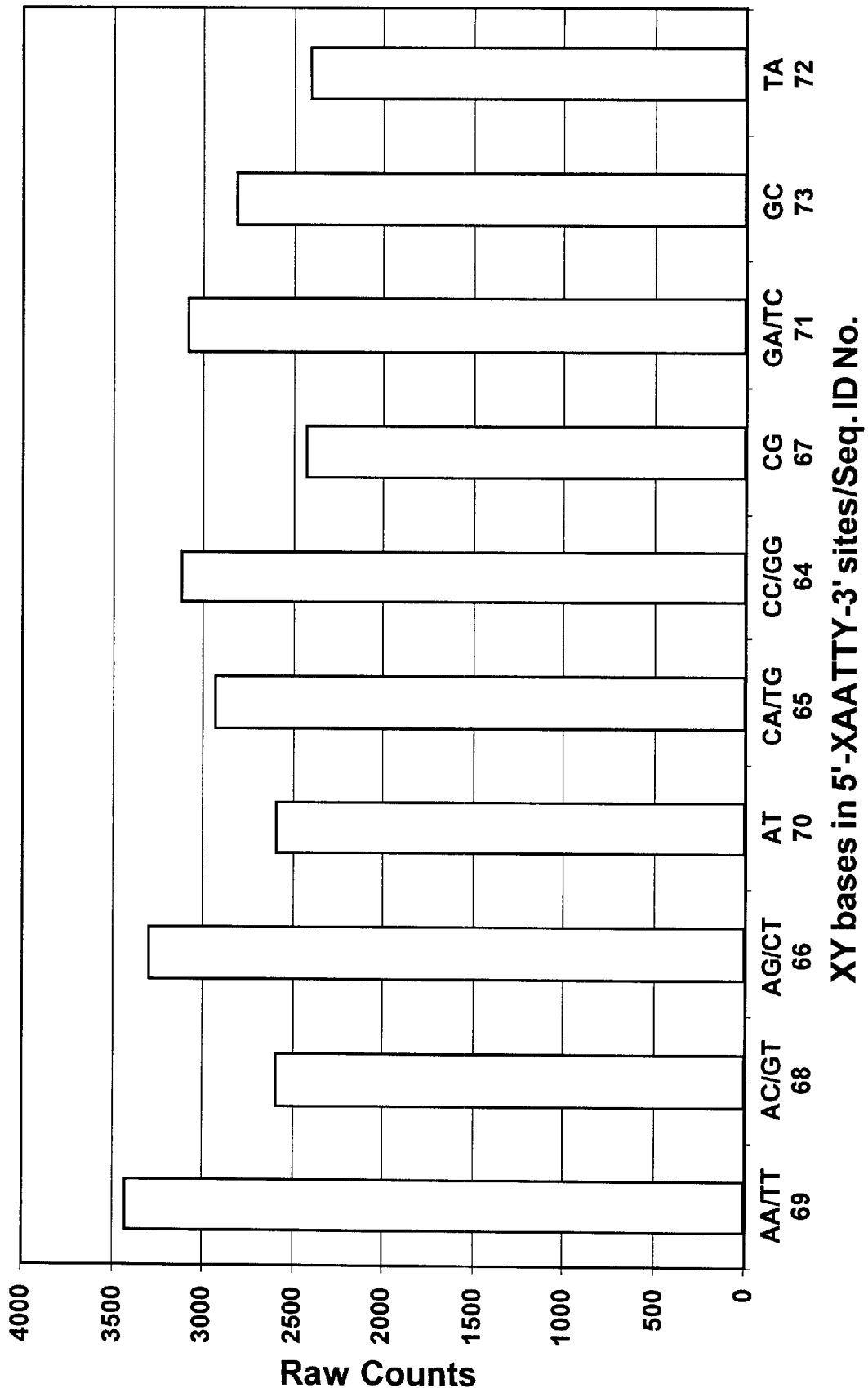

The results, shown in FIGS. 9 and 10, indicate that distamycin is much more sensitive, as expect, to the bases at the edge of the AATT site than is netropsin. The X and Y combinations that competed most effectively for distamycin binding were AA/TT, CA/TG, GA/TC, and TA/TA (i.e., SEQ ID NOS: 69, 65, 71, and 72) (see FIG. 9). The common element in these combinations is an adenine (A) at the Y position, which generates the five base pair sequence 5'-AATTA-3'. One thawould therefore conclude t this is the preferred 5 bp binding site for distamycin.

Figure 11:
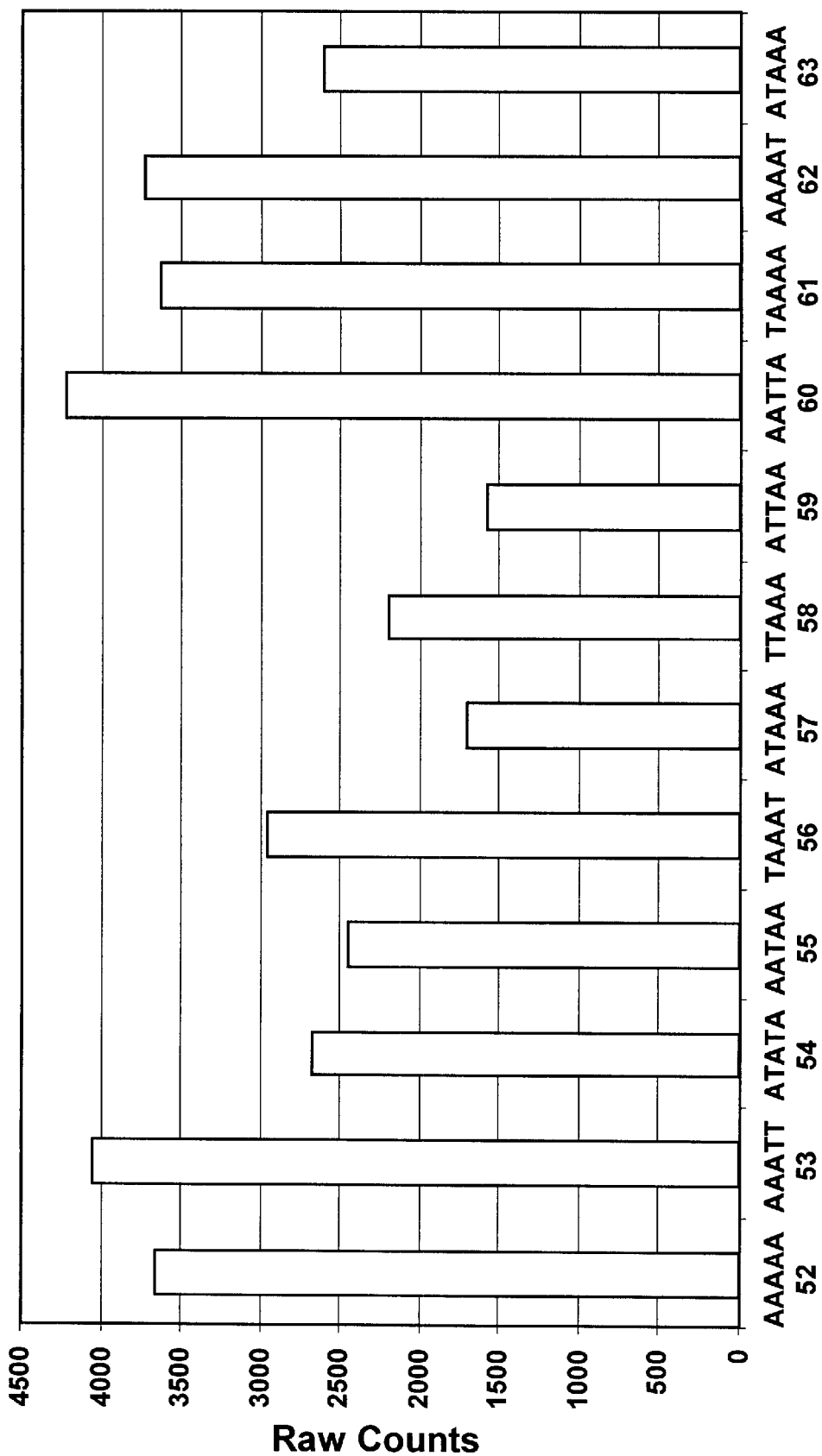
FIGS. 11 and 12 show the increase in fluorescence upon adding competitor oligonucleotides containing various 5-nucleotide A/T motifs to an F/Q indicator duplex having bound distamycin or netropsin, respectively.
Figure 12:
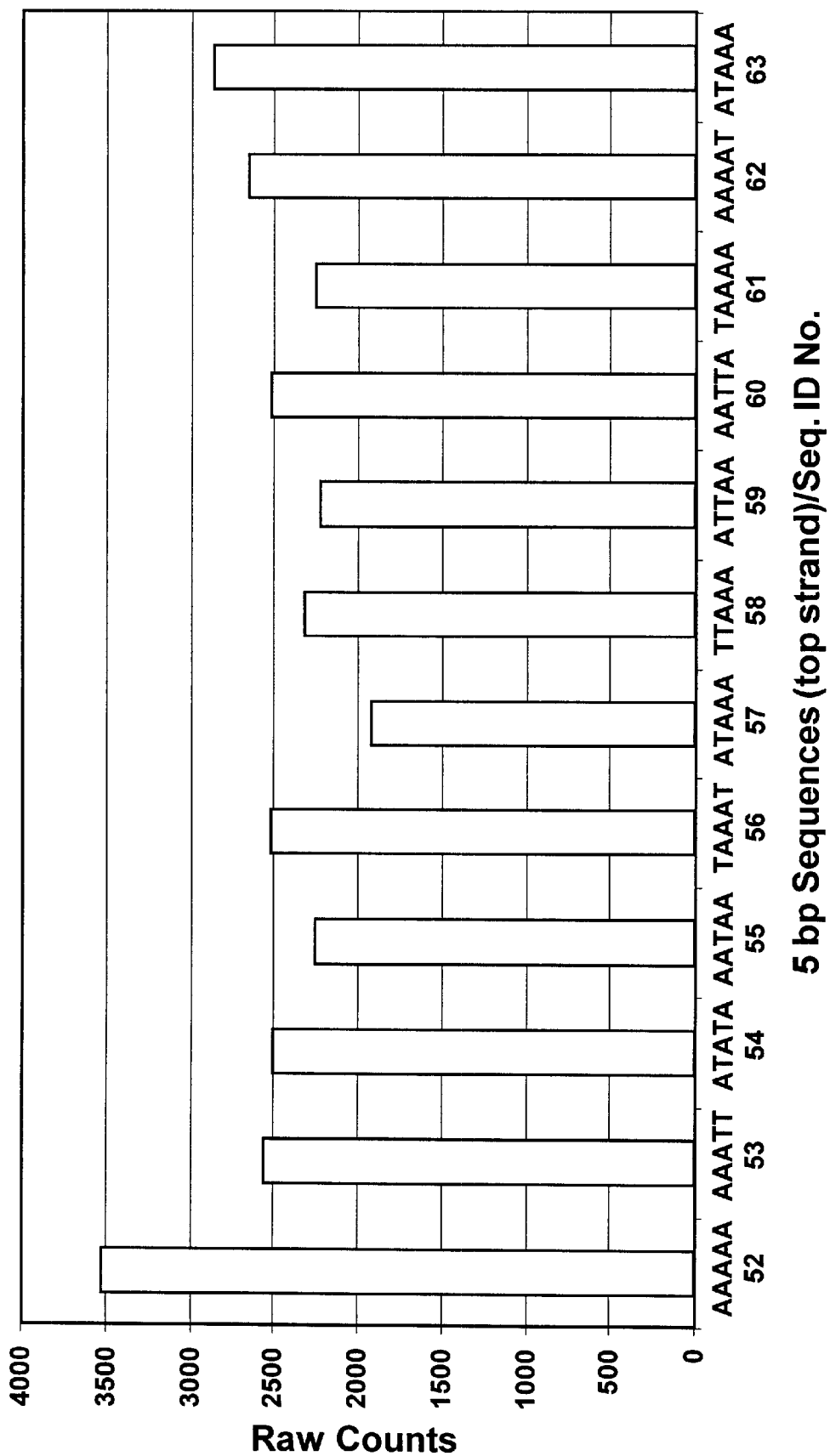

To further support this conclusion, an experiment was done using competitor oligonucleotides containing all possible 5 bp (A+T) binding sites (SEQ ID NOs: 52–63; Table VI). The results, shown in FIG. 11, show that distamycin has relatively strong preferences for the various 5 bp A/T binding sites, and appears to bind most strongly to the site 5'-AATTA-3' (included in SEQ ID NO: 60), confirming the results of the previous example. Netropsin, on the other hand, shows considerably less discrimination for the various 5 bp sites, showing a slight preference for the AAAAA site (included in SEQ ID NO: 52) (FIG. 12).

TABLE VI

Sequences of Competitor Oligonucleotides: 5 bp A + T Sites

| Seq. ID No. | Name | Sequence |
|---|---|---|
| 52 complement | AAAAA | 5'-CCCGAAAAACCG-3' 3'-GGGCTTTTTGGC-5' |
| 53 | AAATT | 5'-CCCGAAATTCCG-3' 3'-GGGCTTTAAGGC-5' |
| 54 | ATATA | 5'-CCCGATATACCG-3' 3'-GGGCTATATGGC-5' |
| 55 | AATAA | 5'-CCCGAATAACCG-3' 3'-GGGCTTATTGGC-5' |
| 56 | TAAAT | 5'-CCCGTAAATCCG-3' 3'-GGGCATTTAGGC-5' |
| 57 | ATAAA | 5'-CCCGATAAACCG-3' 3'-GGGCTATTTGGC-5' |
| 58 | TTAAA | 5'-CCCGTTAAACCG-3' 3'-GGGCAATTTGGC-5' |
| 59 | ATTAA | 5'-CCCGATTAACCG-3' 3'-GGGCTAATTGGC-5' |
| 60 | AATTA | 5'-CCCGAATTACCG-3' 3'-GGGCTTAATGGC-5' |
| 61 | TAAAA | 5'-CCCGTAAAACCG-3' 3'-GGGCATTTTGGC-5' |
| 62 | AAAAT | 5'-CCCGAAAATCCG-3' 3'-GGGCTTTTAGGC-5' |
| 63 | ATAAA | 5'-CCCGATAAACCG-3' 3'-GGGCTATTTGGC-5' |

The sensitivity of the assay is apparent from these examples. The assay also has the advantages of speed and simplicity, as in the direct assay, when compared to previous methods used to obtain comparable information. Further, it is not necessary for the competitive oligonucleotide to be labeled or to attain any particular "quenching" conformation. This feature allows species such as single stranded or folded RNA, which can have highly complex secondary structure, to be tested as easily as linear duplex DNA. Further, as noted for the direct assay, a variety of binding ligands, from single ions to large protein complexes, may be used.

B2. ECL (Electrochemiluminescence) Detection Examples

Three 12-base duplex competitor oligos, containing 1-, 5-, and 8-base stretches of A/T's flanked by G/C sequences, were tested as competitors, using distamycin as the binding ligand and SEQ ID NO: 12 (mixed sequence) as the indicator oligo. The indicator pair was labeled with a 5' ruthenium chelate on one strand and a 3'biotin on the complementary strand, as described above and in Example 14.

Distamycin was premixed at 5 1 $\mu$M with 0.25 nM indicator oligo. The assay was conducted as described in Example 14, using the Igen Origen® apparatus. Ligand binding, which stabilizes the duplexed form of the indicator DNA, results in an increase in the ECL signal. Unlabeled competitor dsDNA (no ruthenium or biotin label) was then added at concentrations ranging from 0.008 to 8.33 $\mu$M, and the decrease in the signal was monitored, as shown in FIG. 13.

Figure 13:
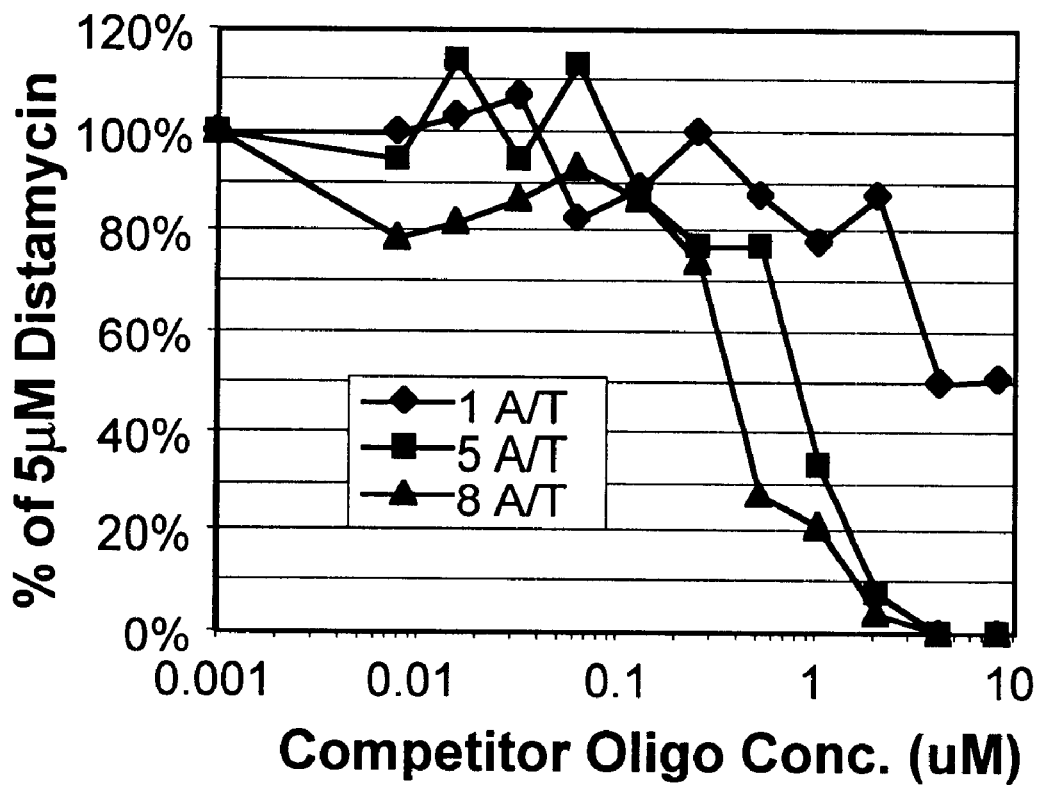
FIG. 13 shows the decrease in ECL signal upon adding unlabeled 12-bp competitor oligonucleotides, containing various length A/T motifs flanked by G/C sequences, to an indicator ECL duplex having bound distamycin.

The competitor sequence having only one A/T base pair, containing no known distamycin binding sites, little competition was observed (see FIG. 13). The competitor oligonucleotidewith a 5 bp A/T site, believed to be an ideal size binding site for distamycin, competed for the ligand with an $IC_{50}$ of 0.9 $\mu$M DNA. The competitor oligonucleotidewith the 8 bp A/T site was shown to compete as well, and gave a lower $IC_{50}$ of 0.35 $\mu$M DNA.

C. Kinetic Strand Displacement: Fluorescence Quenching Example

Figure 14:
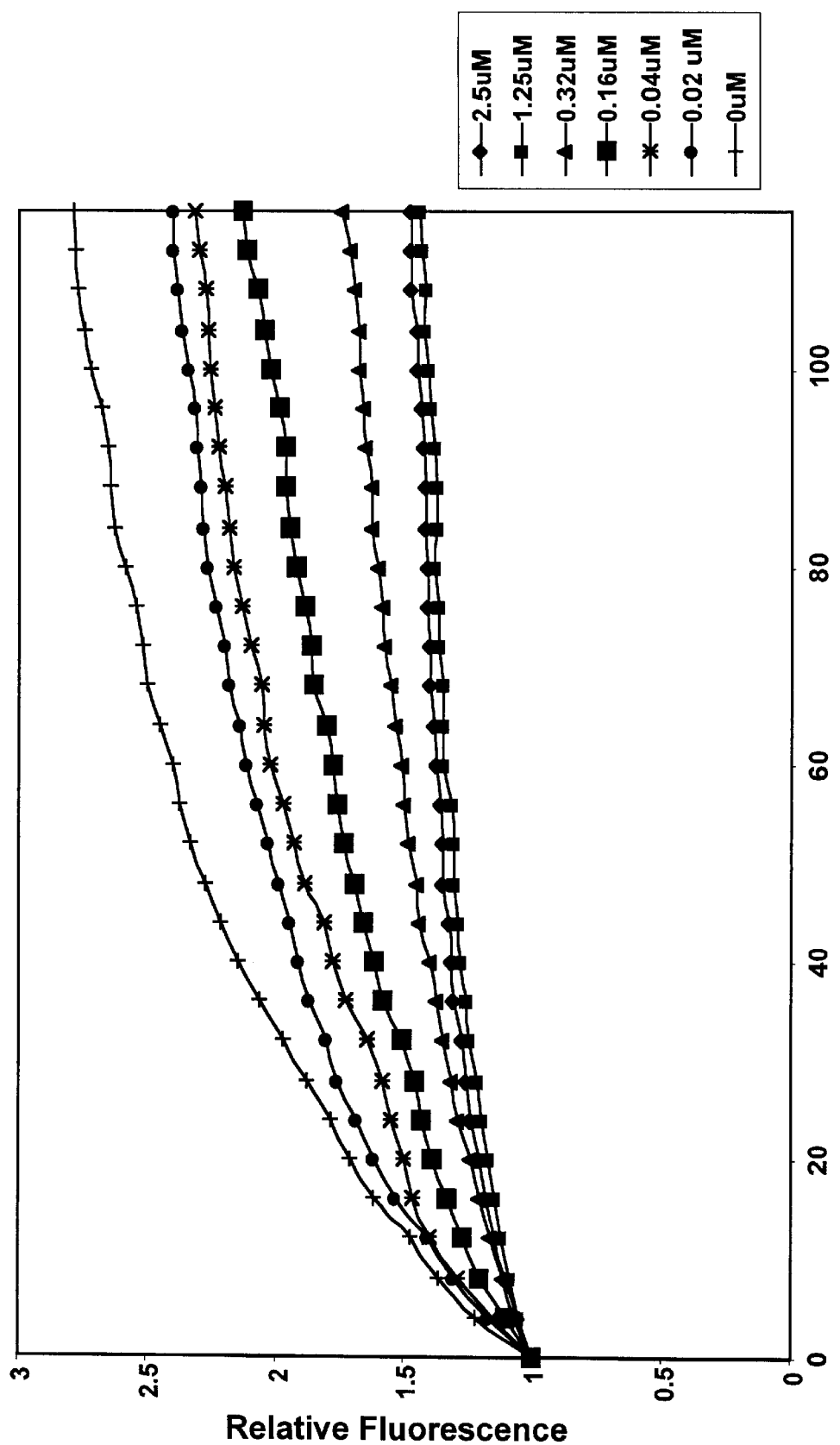
FIG. 14 shows the change in fluorescence in a kinetic strand displacement assay, in the absence of netropsin and in the presence of increasing amounts of netropsin.

Results of a fluorescence quenching strand displacement assay are given in FIG. 14. An F/Q indicator duplex of oligonucleotides having SEQ ID NO: 75 and SEQ ID NO: 76, as shown in Table VI, is formed in the absence of drug (0 $\mu$M curve) and in the presence of increasing amounts of Netropsin (remaining curves). The displacing strand, having SEQ ID NO: 77 (Table VI), is added, and the increase in fluorescence is observed over time. As shown in FIG. 14, fluorescence increased about 175% in 2 hrs in the absence of drug, as the shorter strand (SEQ ID NO: 76) was displaced. About 0.08 $\mu$M drug was effective to detectably slow the rate of displacement, and at 1.25–2.5 $\mu$M, the increase at 2 hrs was reduced to about 40%.

TABLE VII

Oligonucleotides used in Kinetic Strand Displacement Assay

| Seq. ID No. | Sequence |
| --- | --- |
| Strand Displacement Oligos | |
| 75 | 5'-F-CAACGATAGCCGATGTTAGGCAGCTCAC-3' |
| 76 | 3'-Q-GTTGCTATCGGCTACAATCCG-5' |
| 77 | 3'-GTTGCTATCGGCTACAATCCGTCGAGTG-5' |
| Duplex Competition Oligos | |
| 78 | 5'-CAAAAATTTTTC-3' |
| complement | 3'-GTTTTTAAAAAG-5' |
| 79 | 5'-CCCGCGCGCGCC-3' |
| | 3'-GGGCGCGCGCGG-5' |
| 45 | 5'-GGAAGGAAGGAA-3' |
| | 3'-CCTTCCTTCCTT-5' |

Figure 15:
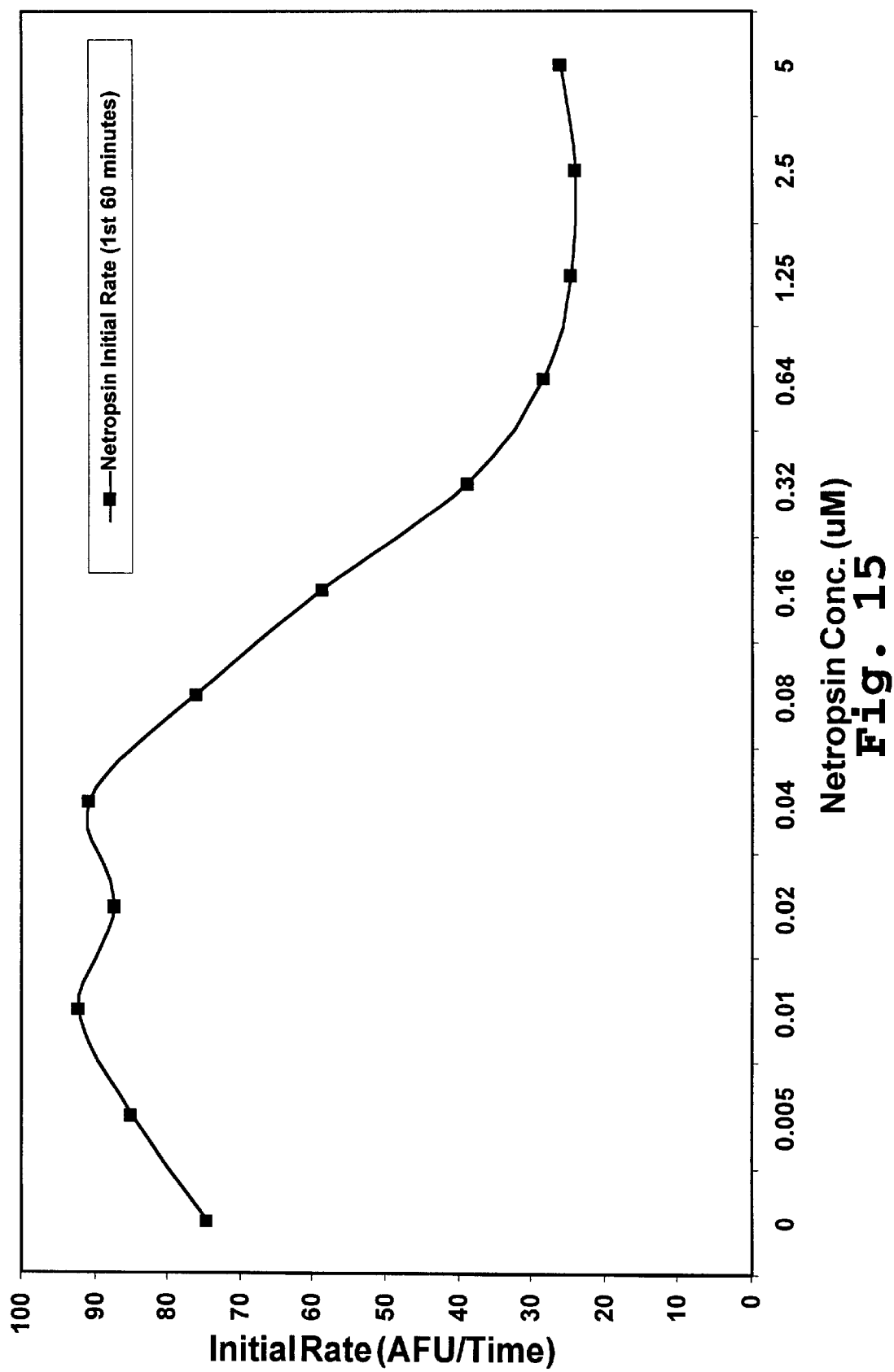
FIG. 15 shows how the initial rate of the displacement reaction of FIG. 11 varies in the presence of increasing amounts of netropsin.

FIG. 15 shows the change in the initial rate of displacement of the shorter oligo, derived from the data of FIG. 14, in the presence of increasing concentrations of netropsin. Again, a notable decrease in displacement is seen at about 0.08 $\mu$M of the drug.

Figure 16:
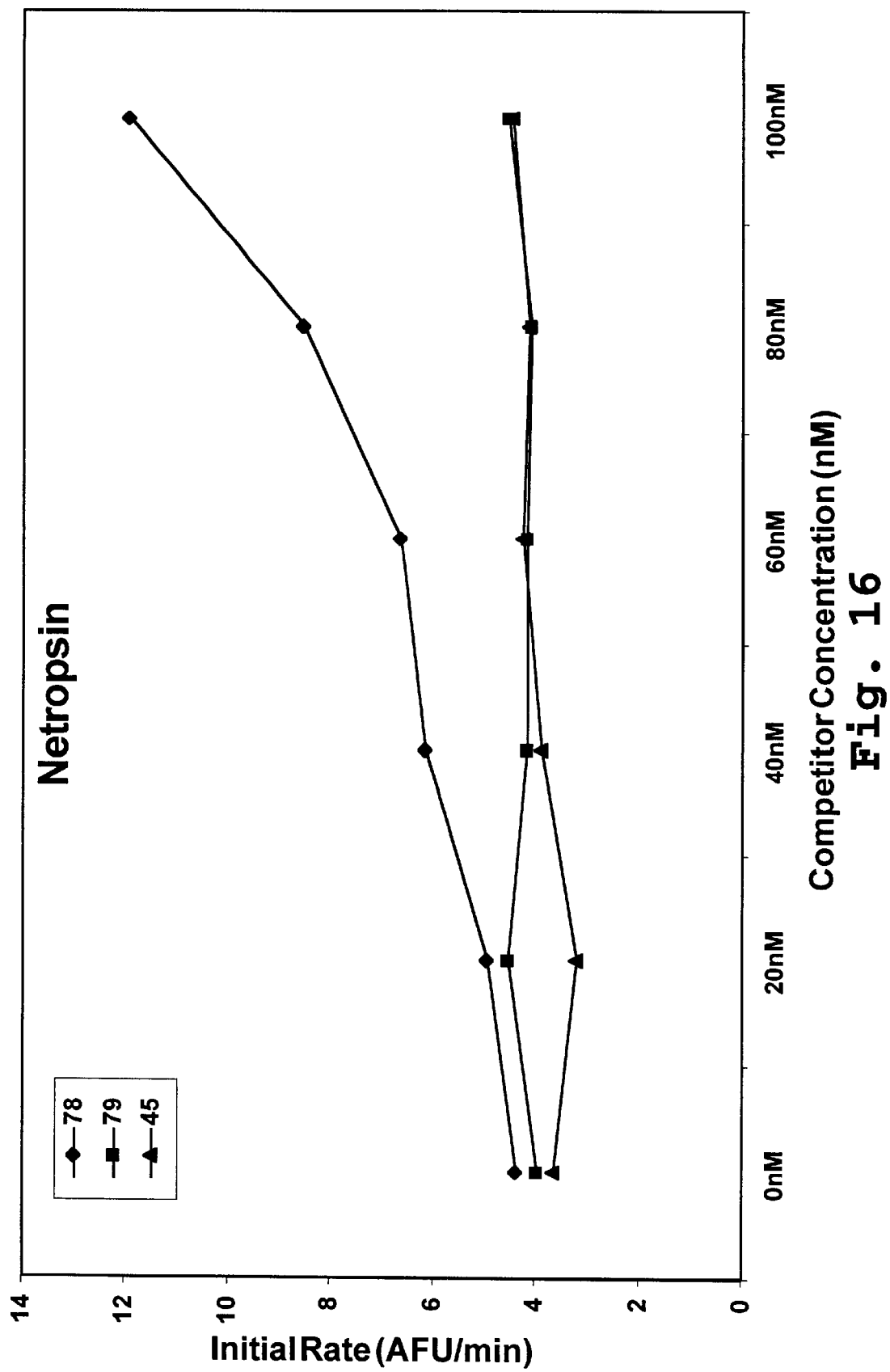
FIG. 16 shows the effect of specific, unlabeled DNA competitors (SEQ ID NO of top strand given in legend) on the initial rate of displacement in the system shown in FIG. 11.

Additional experiments were carried out in which specific, unlabeled DNA competitor duplexes, also shown in Table VII, were added to the assay. FIG. 16 shows the effect of these competitor duplexes on the rate of displacement. The SEQ ID NO. of the top strand of each duplex is given in the Figure legend. Netropsin is believed to bind preferentially to A/T rich regions of DNA, as discussed above. It is expected, therefore, that the A/T rich oligonucleotide, having SEQ ID NO: 78, would competitively bind the drug, prevent it from binding to the indicator oligonucleotides, and thus counteract the effect of the drug in slowing the displacement reaction. Such an effect is shown in FIG. 16, where the rate of displacement is increased by increasing amounts of the A/T rich competitor duplex.

A disadvantage of the displacement assay as compared to the direct assay, above, is that the range of signal is typically narrower, and it tends to show less distinction between stronger and more weakly binding ligands. As noted above, however, the direct assay is best carried out under conditions at which the first and second strands exist in single stranded form in the absence of the ligand. The present assay, however, begins with the first and second strands in duplex form, and does not require comparison of hybridized and fully denatured sequences. Accordingly, displacement assays using longer sequences may be carried out at lower temperatures than would generally be required in a direct assay. The displacement assay is thus useful for determining binding affinities of large ligands, such as proteins.

EXAMPLES

The following examples illustrate but are not intended to limit the invention.

General Procedures (Fluorescence Quenching Detection)

Direct Assays: Direct binding experiments were performed at room temperature (~25° C.) in the following buffer: 10 mM HEPES, pH 7.5, 0.1 mM EDTA, and 10 mM NaCl. Each assay was done in 200 $\mu$l volume in a black flat-bottom microtiter plate. The oligonucleotide concentrations in these experiments were 25 nM for fluorescein labeled oligonucleotide and 40 nM for the Dabcyl™ labeled oligo. In some experiments, transfer RNA was added at concentrations of 10–50 $\mu$g/ml to weaken non-specific interactions between DNA binding drugs and the indicator oligos.

Competition Assays: Competition experiments were generally done in 10 nM HEPES, pH 7.5, 0.1 mM EDTA and 50 mM NaCl. The drug concentration used in the competition assays depends upon the affinity of the drug for a given indicator. For the competition experiments shown, the netropsin and distamycin concentrations used were 0.4 $\mu$M. The amount of competitor oligo used was varied from 0.2 $\mu$M to 1.0 $\mu$M. The data shown is from competition experiments using 0.4 $\mu$M unlabeled duplex competitors (see Tables III–VI for the sequences of the competitor oligos).

Examples 1–2
Direct Binding Assays with Netropsin and Actinomycin

According to the general method described above, increasing amounts of netropsin or actinomycin, respectively, were added to mixtures of selected F/Q indicator oligonucleotide pairs, whose sequences are shown in the legends of FIGS. 1 and 3. The sequence of the "F" strand of each pair is given in the legends, along with single stranded controls, as indicated. The Figures show the level of fluorescence observed, relative to a control having no added drug, for each indicator pair (or single strand) as the level of added drug was increased. In these experiments, transfer RNA was added at concentrations of 10–50 μg/ml to weaken non-specific interactions between DNA binding drugs and the indicator oligos.

Example 3
Direct Binding Assay with Bekanomycin

According to the general method described above, increasing amounts of bekanomycin were added to mixtures of selected F/Q indicator oligonucleotide pairs, whose sequences are shown in the legend of FIG. 6. The Figure shows the level of fluorescence observed, relative to a control having no added drug, for each indicator pair (or single strand) as the level of added drug was increased.

Example 4
Direct Binding Assays with Netropsin

In this experiment, the assay was carried out in the same manner as Example 1, but in the absence of transfer RNA. The level of fluorescence observed, relative to control, with increasing amounts of drug is shown in FIG. 3D. The effect of non-specific binding, relative to FIG. 3A, can be seen at higher levels of added drug.

Examples 5–6
Competition Assays with Distamycin and Netropsin

According to the general procedure above, a mixture was formed of 0.4 μM drug and A/T rich F/Q indicator duplex (5'-CTTTATTATTTT-3'; SEQ ID NO: 2, and its complement). The assay employed 25 nM of the "F" sequence (SEQ ID NO: 2) and 40 nM of the complementary "Q" sequence. An unlabeled competitor duplex, selected from those whose sequences are given in Table II, was added at a 0.4 μM concentration, and the change in fluorescence was noted. Results for a series of competitor sequences are shown in FIG. 6.

Examples 7–8
Competition Assays with Distamycin and Netropsin: Poly-A and Poly-AT Sequences The assays described in Examples 5–6 were repeated, using unlabeled competitor duplexes with varying lengths of AA and A/T sequence motifs, whose sequences are given in Table IV. Changes in fluorescence of the indicator duplex/ drug mixtures on adding each competitor oligonucleotide are given in FIGS. 7 and 8.

Examples 9–10
Competition Assays with Distamycin and Netropsin: XAATTY Sequences The assays described in Examples 5–6 were repeated, using unlabeled competitor duplexes with all combinations of bases flanking an AATT site, whose sequences are given in Table V. Changes in fluorescence of the indicator duplex/ drug mixtures on adding each competitor oligo are given in FIGS. 9 and 10.

Example 11
Competition Assays with Netropsin: 5 bp Poly(AT) Sequences

The assays described in Examples 5–6 were repeated, using unlabeled competitor duplexes with all combinations of 5 bp A/T sequences, whose sequences are given in Table VI. Changes in fluorescence of the indicator duplex/ netropsin mixture on adding each competitor oligonucleotide are given in FIG. 12.

Example 12
Kinetic Strand Displacement Assay with Netropsin

A mixture was formed of 60 nM of a fluorescein labeled 28-nucleotide strand having SEQ ID NO: 75 (Table VI) and 90 nM of a Dabcyl™-labeled 21-nucleotide quenching strand (SEQ ID NO: 76) in a buffer containing 20 mM HEPES, pH 7.5, 0.1 mM EDTA, and 30 mM NaCl. The control experiment contained no added drug; for subsequent experiment, increasing amounts of netropsin were added. To start the displacement reaction, the displacing strand (SEQ ID NO: 77) was added at concentrations of 35 nM to 60 nM. The fluorescence of the system was then monitored every 5 minutes for 90 to 120 minutes. Results for the control experiment and experiments containing 0.02 μM to 2.5 μM netropsin are shown in FIG. 14.

The initial rate of the displacement reaction was calculated from plots of fluorescence vs. time as the slope of the fluorescence curve from 0 to 60 minutes. This data is shown in FIG. 15.

Additional experiments were carried out in which specific, unlabeled DNA competitor duplexes, whose sequences are shown in Table VII, were added to the assay mixture. FIG. 16 shows the effect of these competitor strands on the rate of displacement, as determined by change in fluorescence of the system.

Example 13
Nucleic Acid Ligand Detection by SPA

Indicator oligonucleotides as shown in Table 1 were used in this assay, as shown in Table II and FIGS. 4A–E. One strand of each duplex was labeled with biotin at the 5'-end, and the complementary strand was 3'-labeled with $^{33}P$. The two complementary strands were incubated with streptavidin-coated SPA beads (Amersham, Arlington Heights, Ill.) at room temperature in a buffer containing 20 mM HEPES, pH 7.5, 0.1 mM EDTA, and 20 mM NaCl. In the absence of ligand, and under these conditions, the oligonucleotides exist in single-stranded conformation. As a result, the oligonucleotide containing the radioactive label is not in close proximity to the SPA bead, and the light given off by the beads is low, i.e., at background. As a duplex-stabilizing ligand is added, the radioactive $^{33}P$ is brought into close proximity to the SPA bead, and the light emitted from the SPA bead increases. Accordingly, each of five known DNA-binding compounds was added in increasing concentrations, and the effect on scintillation count was observed, giving the results shown in FIGS. 4A–E.

The assay can be performed in commercially available high throughput screening systems, thus providing a high throughput method for finding novel nucleic acid binding compounds. In this system, a series of different oligonucleotide indicator pairs are placed in wells on a microtiter plate, and the assays are performed, using a series of candidate ligands. An exemplary assay utilizes a panel of indicator oligonucleotides such as shown in Table II; i.e. A/T rich DNA indicator oligonucleotide (CTTTATTATTTT; SEQ ID NO: 2), a G/C rich DNA indicator (CCGCGCC; SEQ ID NO: 6), a mixed sequence DNA indicator (GCGGTATTT; SEQ ID NO: 12), and an RNA indicator (CUAGAUCUGA; SEQ ID NO: 23), and the respective complements, in which one strand is biotinylated and the complementary strand is end-labeled with $^{33}P$. A ligand is titrated into wells containing each of the oligonucleotide indicator pairs, and the increase in light output is measured.

Example 14
Binding Assay Using ECL Detection

An indicator pair of oligonucleotides, having the sequence SEQ ID NO: 12 and complement, were labeled with a 5' ruthenium (bipy) chelate on one strand, as described in U.S. Pat. No. 5,635,347 and references cited therein, and with a 3' biotin on the complementary strand. The labeled oligonucleotides were combined at 0.5 μM and 3 μg/ml tRNA in 150 μl HEN10 buffer (100 mM HEPES, pH 7.2, 10 mM NaCl and 1 mM EDTA). The test ligand, diluted in 30 μl HEN10 to 10×the desired final concentration, was added, and the was mixture incubated for 30 min at RT. The biotin-labeled oligonucleotide was captured with 0.005 mg streptavidin A coated para-magnetic beads (Dynal AS, Oslo, Norway) added in 120 μl HEN10. The mixture was mixed and incubated for 30 min at room temperature. The biotinylated strand of DNA was captured on the bead surface, and any ruthenium captured by the streptavidin via drug-stabilized hybridization of the indicator duplex was quantified with the IGEN Origen™ analyzer. The sample tubes were placed in a vortexing carousel to keep the beads in suspension prior to sampling. A 175 μl volume of the reaction mixture was pumped into a flow cell over 6 seconds, and the beads were captured by a magnet onto a platinum electrode. The beads were washed for 6 seconds with the IGEN Assay Buffer, which contains the second oxidation reaction component, tripropyl amine. Voltage was applied (POP set to 0 mV). Charging of the electrode (generally less than two volts) triggers light production from the ruthenium label. The light emitted was measured in a photomultiplier tube and digitally stored.

Results of a direct binding assay using this detection method were shown in FIGS. 5A and 5B; results of a competitive assay were shown in FIG. 13.

What is claimed is:

1. A method of determining the relative binding affinities of a ligand to different oligonucleotide sequences, comprising (i) forming a mixture of a first indicator pair of oligonucleotides, comprising a first oligonucleotide, which comprises a first group effective to produce a detectable signal, and a second oligonucleotide, which comprises a second group, such that in the presence of said second group said signal is detectably altered upon hybridization of said first and second oligonucleotides, and in the absence of said second group said signal would not be detectably altered upon such hybridization;

wherein said mixture is formed under conditions such that, in the absence of said ligand, said oligonucleotides exist primarily in single-stranded form;

(ii) observing said signal from said mixture in the absence of said ligand;

(iii) adding said ligand to said mixture;

(iv) observing said signal from said mixture in the presence of said ligand;

(v) comparing said effect with that observed upon carrying out steps (i)–(iv) with a second indicator pair of oligonucleotides; and (vi) determining the relative binding affinities of said ligand to said first and second indicator pairs by comparing said effects.

2. The method of claim 1, wherein said ligand is added to said mixture in increasing concentrations, and step (iv) comprises observing said signal in the presence of increasing concentrations of said ligand.

3. The method of claim 2, wherein said mixture is held at a substantially constant temperature as said ligand is added.

4. The method of claim 3, wherein said temperature is at or near room temperature.

5. The method of claim 1, wherein said ligand is selected from a metal ion, a small organic or inorganic molecule, a protein, and a multi-protein complex.

6. The method of claim 1, wherein said first group is attached at the 5'-end or 3'-end of the first oligonucleotide, and said second group is attached at the 3'-end or 5'-end, respectively, of the second oligonucleotide.

7. The method of claim 1, wherein said first group is a radiation emitting group, and said second group is effective to absorb radiation emitted by said first group.

8. The method of claim 1, wherein said first group comprises a scintillant, and said second group is a radioactive group.

9. The method of claim 1, wherein said first group is a chemiluminescent group.

10. The method of claim 1, wherein said second group is effective to alter the proximity of said duplex to a source which is effective to stimulate or modulate the production of said signal from said first group, and said stimulation or modulation is proximity-dependent.

11. The method of claim 10, wherein said second group is a binding group effective to bind to a surface.

12. A method of determining the binding affinity of a ligand to an oligonucleotide sequence, comprising
 (i) providing first and second oligonucleotides, which are effective to hybridize by Watson-Crick base pairing to form a duplex;
 wherein said first oligonucleotide comprises a first group effective to produce a detectable signal,
 and said second oligonucleotide comprises a second group, such that in the presence of said second group said signal is detectably altered upon hybridization of said first and second oligonucleotides, and in the absence of said second group said signal would not be detectably altered upon such hybridization;
 (ii) forming a mixture of said oligonucleotides under conditions such that, in the absence of said ligand, said oligonucleotides exist primarily in single-stranded form;
 (iii) observing said signal from said mixture in the absence of said ligand;
 (iv) adding said ligand to said mixture;
 (v) observing said signal from said mixture in the presence of said ligand, and
 (vi) determining the binding affinity of said ligand to said first and second oligonucleotides by comparing the observed signals,
 wherein said first group is an electrochemiluminescent group.

13. The method of claim 12, wherein said second group is effective to alter the proximity of said duplex to a source which is effective to stimulate or modulate the production of said signal from said first group, said stimulation or modulation being proximity-dependent;
 said second group being a binding group effective to bind to a surface which comprises a metallic surface to which a voltage may be applied, or a magnetic surface effective to adhere to such a metallic surface.

14. A method of determining the relative binding affinities of a ligand to different oligonucleotide sequences, comprising
 (i) forming a mixture of a first indicator pair of oligonucleotides, comprising (a) a first oligonucleotide, which comprises a first group effective to produce a detectable signal, and (b) a second oligonucleotide, effective to hybridize with said first oligonucleotide by Watson-Crick base pairing to form a duplex, and which comprises a second group, such that in the presence of said second group said signal is detectably altered upon hybridization of said first and second oligonucleotides, and in the absence of said second group said signal would not be detectably altered upon such hybridization;
 wherein said first and second oligonucleotides differ in length, such that said duplex has an overhang region,
 (ii) forming a duplex of said oligonucleotides,
 (iii) adding an unlabeled displacement strand which is effective to displace one of said oligonucleotides from said duplex in the absence of said ligand, thereby altering said signal;
 (iv) observing said signal upon said adding, in the absence and in the presence of said ligand;
 (v) comparing the observed signals with those observed upon carrying out steps (i)–(iv) with a second indicator pair; and
 (vi) determining the relative binding affinities of said ligand to said first and second indicator pairs by comparing the observed signals.

15. The method of claim 14, wherein said forming, adding and observing steps are carried out at a substantially constant temperature.

16. The method of claim 15, wherein said temperature is at or near room temperature.

17. The method of claim 14, wherein said overhang region is about 4–20 nucleotides in length.

18. The method of claim 14, further comprising the steps of
 (vii) adding a competitor oligonucleotide, and
 (viii) observing the effect of such adding on said signal.

19. The method of claim 18, wherein said competitor oligonucleotide is selected from the group consisting of a duplex DNA, a duplex RNA, a duplex DNA/RNA hybrid, and a single stranded oligonucleotide.

20. The method of claim 19, wherein said single stranded oligonucleotide is capable of folding into a double stranded secondary structure.

21. A method of determining the relative binding affinities of a ligand to different oligonucleotide sequences, comprising
 (i) providing a first indicator pair or oligonucleotides, comprising first and second oligonucleotides, which are effective to hybridize by Watson-Crick base pairing to form a duplex;
 wherein said first oligonucleotide comprises a first group effective to produce a detectable signal,
 and said second oligonucleotide comprises a second group, such that in the presence of said second group said signal is detectably altered upon hybridization of said first and second oligonucleotides, and in the absence of said second group said signal would not be detectably altered upon such hybridization;
 (ii) forming an indicator duplex of said oligonucleotides, having bound thereto said ligand, which is effective to stabilize said duplex;
 (iii) adding a competitor oligonucleotide,
 (iv) observing the effect of such adding on the signal;
 (v) comparing said effect with that observed upon carrying out steps (ii)–(iv) with a second competitor oligonucleotide; and
 (vi) determining the relative binding affinities of said ligand to said first and second competitor oligonucleotides by comparing said effects.

22. The method of claim 21, wherein, in step (ii), said indicator duplex is formed under conditions such that, in the absence of said ligand, said first and second oligonucleotides would exist primarily in single-stranded form.

23. The method of claim 21, wherein said adding and observing steps are carried out at a substantially constant temperature.

24. The method of claim 23, wherein said temperature is at or near room temperature.

25. The method of claim 21, wherein said competitor oligonucleotide is unlabeled.

26. The method of claim 21, wherein said competitor oligonucleotide is selected from the group consisting of a duplex DNA, a duplex RNA, a duplex DNA/RNA hybrid, and a single stranded oligonucleotide.

27. The method of claim 26, wherein said single stranded oligonucleotide is capable of folding into a double stranded secondary structure.

28. The method of claim 21, wherein said first group is attached at the 5'-end or 3'-end of the first oligonucleotide, and said second group is attached at the 3'-end or 5'-end, respectively, of the second oligonucleotide.

29. The method of claim 21, wherein said first group is a radiation emitting group, and said second group is effective to absorb radiation emitted by said first group.

30. The method of claim 21, wherein said first group comprises a scintillant, and said second group is a radioactive group.

31. The method of claim 21, wherein said first group is a chemiluminescent group.

32. The method of claim 21, wherein said ligand is selected from a metal ion, a small organic or inorganic molecule, a protein, and a multi-protein complex.

33. A method of determining the relative binding affinities of a ligand to different oligonucleotide sequences, comprising (i) providing first and second oligonucleotides, which are effective to hybridize by Watson-Crick base pairing to form a duplex;

wherein said first oligonucleotide comprises a first group effective to produce a detectable signal, and said second oligonucleotide comprises a second group, such that in the presence of said second group said signal is detectably altered upon hybridization of said first and second oligonucleotides, and in the absence of said second group said signal would not be detectably altered upon such hybridization;

(ii) forming an indicator duplex of said oligonucleotides, having bound thereto said ligand, which is effective to stabilize said duplex;

(iii) adding a competitor oligonucleotide, (iv) observing the effect of such adding on the signal, and (v) determining the relative binding affinities of said ligand to said first and second oligonucleotides by comparing the observed signals wherein said first group is an electrochemiluminscent group.

wherein said first group is an electrochemiluminescent group.

34. The method of claim 21, wherein said second group is effective to alter the proximity of said duplex to a source which is effective to stimulate or modulate the production of said signal from said first group, and said stimulation or modulation is proximity-dependent.

35. The method of claim 33, wherein said second group is a binding group effective to bind to a surface.

36. The method of claim 33, wherein said second group is effective to alter the proximity of said duplex to a source which is effective to stimulate or modulate the production of said signal from said first group, said stimulation or modulation being proximity-dependent;

said second group being a binding group effective to bind to a surface which comprises a metallic surface to which a voltage may be applied, or a magnetic surface effective to adhere to such a metallic surface.

37. A method of determining the relative binding affinities of a plurality of ligands, comprising a first ligand and a second ligand, to an oligonucleotide sequence, comprising (i) providing first and second oligonucleotides, which are effective to hybridize by Watson-Crick base pairing to form a duplex;

wherein said first oligonucleotide comprises a first group effective to produce a detectable signal, and said second oligonucleotide comprises a second group, such that in the presence of said second group said signal is detectably altered upon hybridization of said first and second oligonucleotides, and in the absence of said second group said signal would not be detectably altered upon such hybridization;

(ii) forming a mixture of said oligonucleotides under conditions such that, in the absence of ligand, said oligonucleotides exist primarily in single-stranded form;

(iii) observing said signal from said mixture in the absence of ligand;

(iv) adding said first ligand to said mixture;

(v) observing said signal from said mixture in the presence of said first ligand;

(vi) comparing said effect with that observed upon carrying out steps (ii)–(v) with said second ligand; and (vi) determining the relative binding affinities of said first and second ligands to said indicator pair by comparing said effects.

38. A method of determining the relative binding affinities of a plurality of ligands, comprising a first ligand and a second ligand, to an oligonucleotide sequence, comprising (i) forming a mixture of an indicator pair of oligonucleotides, comprising (a) a first oligonucleotide, which comprises a first group effective to produce a detectable signal, and (b) a second oligonucleotide, effective to hybridize with said first oligonucleotide by Watson-Crick base pairing to form a duplex, and which comprises a second group, such that in the presence of said second group said signal is detectably altered upon hybridization of said first and second oligonucleotides, and in the absence of said second group said signal would not be detectably altered upon such hybridization;

wherein said first and second oligonucleotides differ in length, such that said duplex has an overhang region, (ii) forming a duplex of said oligonucleotides, (iii) adding an unlabeled displacement strand which is effective to displace one of said oligonucleotides from said duplex in the absence of ligand, thereby altering said signal;

(iv) observing said signal upon said adding, in the absence and in the presence of said first ligand;

(v) comparing the observed signals with those observed upon carrying out steps (ii)–(iv) with said second ligand; and (vi) determining the relative binding affinities of said ligands to said indicator pair by comparing the observed signals.

* * * * *